US010981713B2

(12) United States Patent
Genosar

(10) Patent No.: US 10,981,713 B2
(45) Date of Patent: Apr. 20, 2021

(54) PACKAGED PRODUCTS, INSERTS AND COMPARTMENTS FOR ASEPTIC MIXING OF SUBSTANCES, ALONG WITH METHODS FOR USE THEREWITH

(71) Applicant: Aktivax, Inc., Broomfield, CO (US)

(72) Inventor: Amir Genosar, Boulder, CO (US)

(73) Assignee: Aktivax, Inc., Broomfield, CO (US)

( * ) Notice: Subject to any disclaimer, the term of this patent is extended or adjusted under 35 U.S.C. 154(b) by 132 days.

(21) Appl. No.: 15/495,882

(22) Filed: Apr. 24, 2017

(65) Prior Publication Data
US 2018/0072480 A1 Mar. 15, 2018

Related U.S. Application Data

(63) Continuation of application No. 14/290,664, filed on May 29, 2014, now abandoned, which is a continuation of application No. 13/144,184, filed as application No. PCT/US2010/020824 on Jan. 12, 2010, now abandoned.

(60) Provisional application No. 61/261,315, filed on Nov. 14, 2009, provisional application No. 61/143,971, filed on Jan. 12, 2009.

(51) Int. Cl.
| B65D 81/32 | (2006.01) |
| A61J 1/20 | (2006.01) |
| A61M 5/24 | (2006.01) |
| B65D 25/08 | (2006.01) |
| A61M 5/32 | (2006.01) |

(52) U.S. Cl.
CPC ............ *B65D 81/32* (2013.01); *B65D 25/08* (2013.01); *B65D 81/3205* (2013.01); *B65D 81/3233* (2013.01); *B65D 81/3266* (2013.01)

(58) Field of Classification Search
CPC .......... A61J 1/202; A61J 1/201; A61J 1/2024; Y10S 215/08; B65D 81/3233; B65D 81/3205; B65D 81/3266; B65D 81/32; B65D 25/08
USPC .................................................. 206/219, 221
See application file for complete search history.

(56) References Cited

U.S. PATENT DOCUMENTS

| 3,156,369 A | 11/1964 | Bowes et al. |
| 3,489,306 A | 1/1970 | Bubb |
| 3,756,390 A | 9/1973 | Abbey et al. |
| 3,917,063 A | 11/1975 | Chibret et al. |
| 3,964,643 A | 6/1976 | Morane et al. |

(Continued)

FOREIGN PATENT DOCUMENTS

| EP | 050975 | 10/1991 |
| JP | 200238858 | 9/2000 |

(Continued)

OTHER PUBLICATIONS

International Search Report and Written Opinion for PCT/US2010/020824 dated Aug. 17, 2010, 14 pages.

(Continued)

*Primary Examiner* — Andrew D Perreault
(74) *Attorney, Agent, or Firm* — Holzer Patel Drennan

(57) ABSTRACT

A package comprising a container for holding a first substance, and a product insert for holding a second substance, at least partially inserted info said container, and where the first product and the second product can be allowed to merge by external manipulation of said package. Packaged products and methods are also provided.

6 Claims, 17 Drawing Sheets

(56) References Cited

U.S. PATENT DOCUMENTS

| | | | |
|---|---|---|---|
| 4,561,543 A | | 12/1985 | Thompson |
| 4,903,865 A | | 2/1990 | Janowitz |
| 5,169,388 A | | 12/1992 | McPhee |
| 5,352,196 A | | 10/1994 | Haber et al. |
| 5,383,579 A | * | 1/1995 | Lanfranconi ......... A61J 1/2093 |
| | | | 222/129 |
| 5,409,141 A | | 4/1995 | Kikuchi et al. |
| 5,423,421 A | * | 6/1995 | Inoue ....................... A61J 1/00 |
| | | | 206/219 |
| 5,950,819 A | | 9/1999 | Sellars |
| 5,954,703 A | | 9/1999 | Golub |
| 6,152,296 A | | 11/2000 | Shih |
| 6,364,105 B1 | | 4/2002 | Yacko et al. |
| 6,921,087 B2 | | 7/2005 | Takahashi et al. |
| 7,243,787 B2 | * | 7/2007 | Iwasa ....................... A61J 1/10 |
| | | | 206/219 |
| 2005/0072442 A1 | | 4/2005 | Licari et al. |
| 2009/0152267 A1 | | 6/2009 | May et al. |

FOREIGN PATENT DOCUMENTS

| | | |
|---|---|---|
| JP | 200400509 | 1/2004 |
| WO | 1993-021890 | 11/1993 |
| WO | WO 0029305 A2 | 5/2000 |
| WO | 2010-081174 | 7/2010 |

OTHER PUBLICATIONS

International Preliminary Report on Patentability for PCT/US2010/020824 dated Jul. 12, 2011, 11 pages.

* cited by examiner (Substance insert removed)

(Pre-use)

(Reconstituted)

(substance insert removed)

(Pre-use)

(Reconstituted)

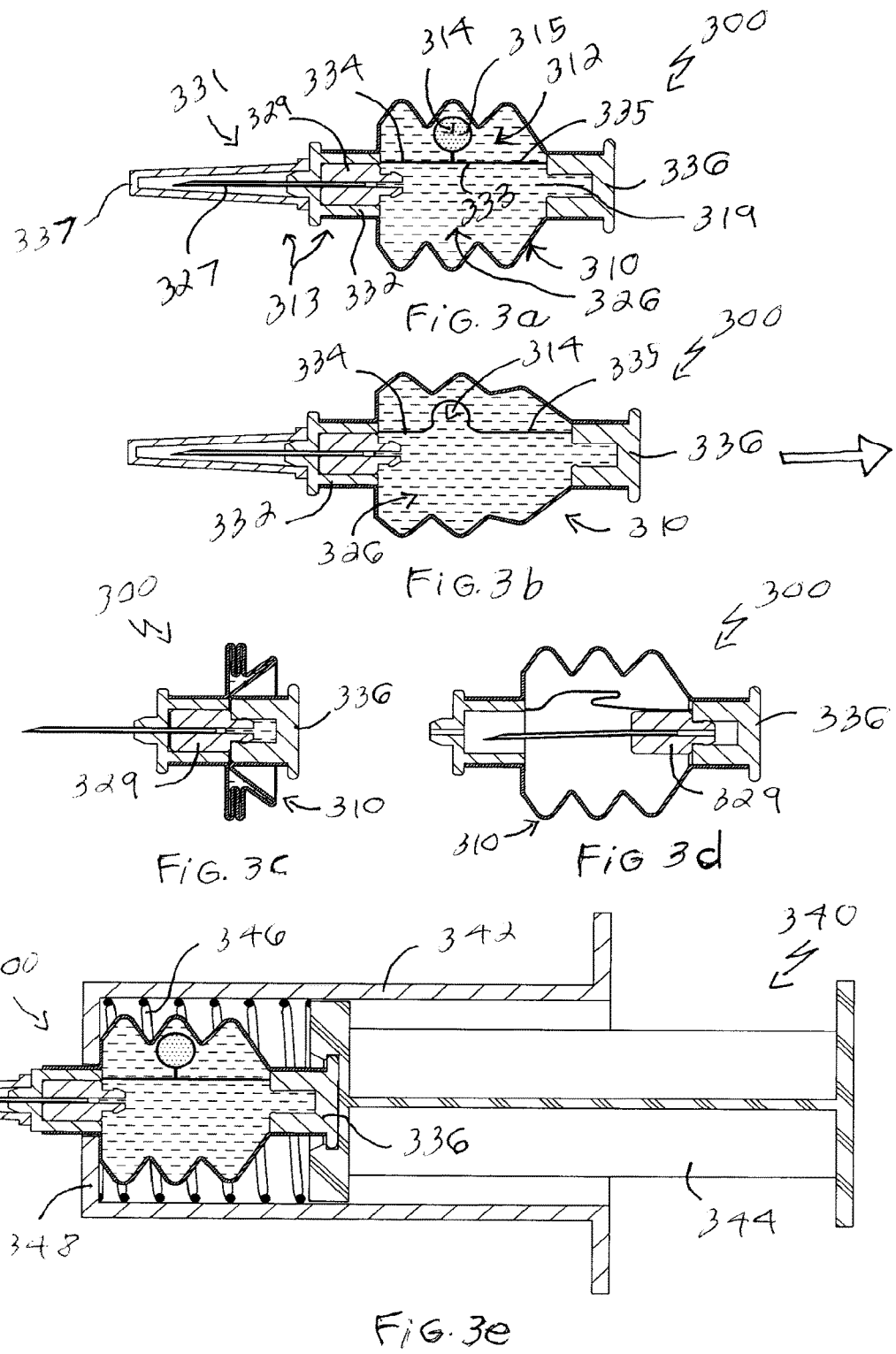

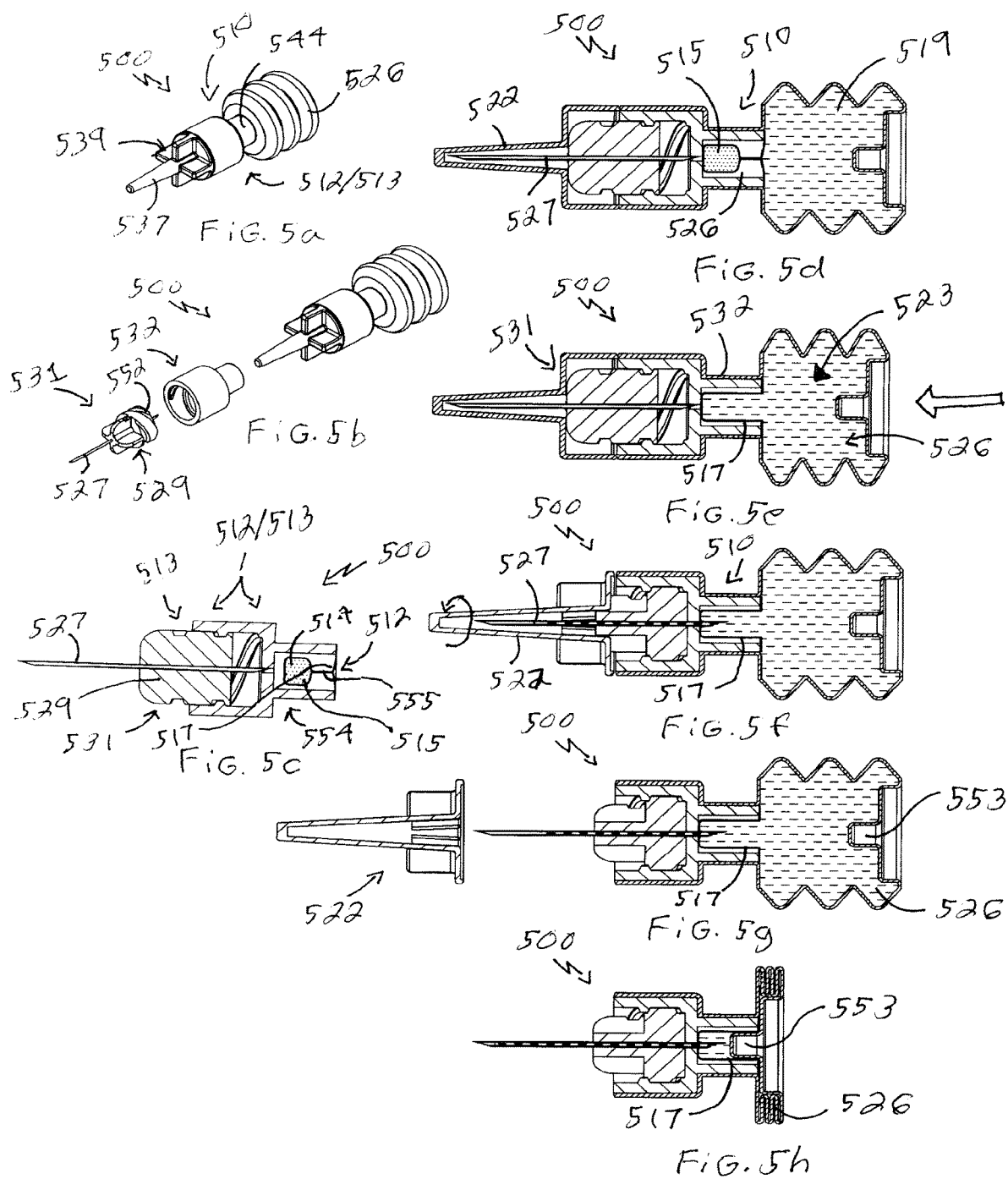

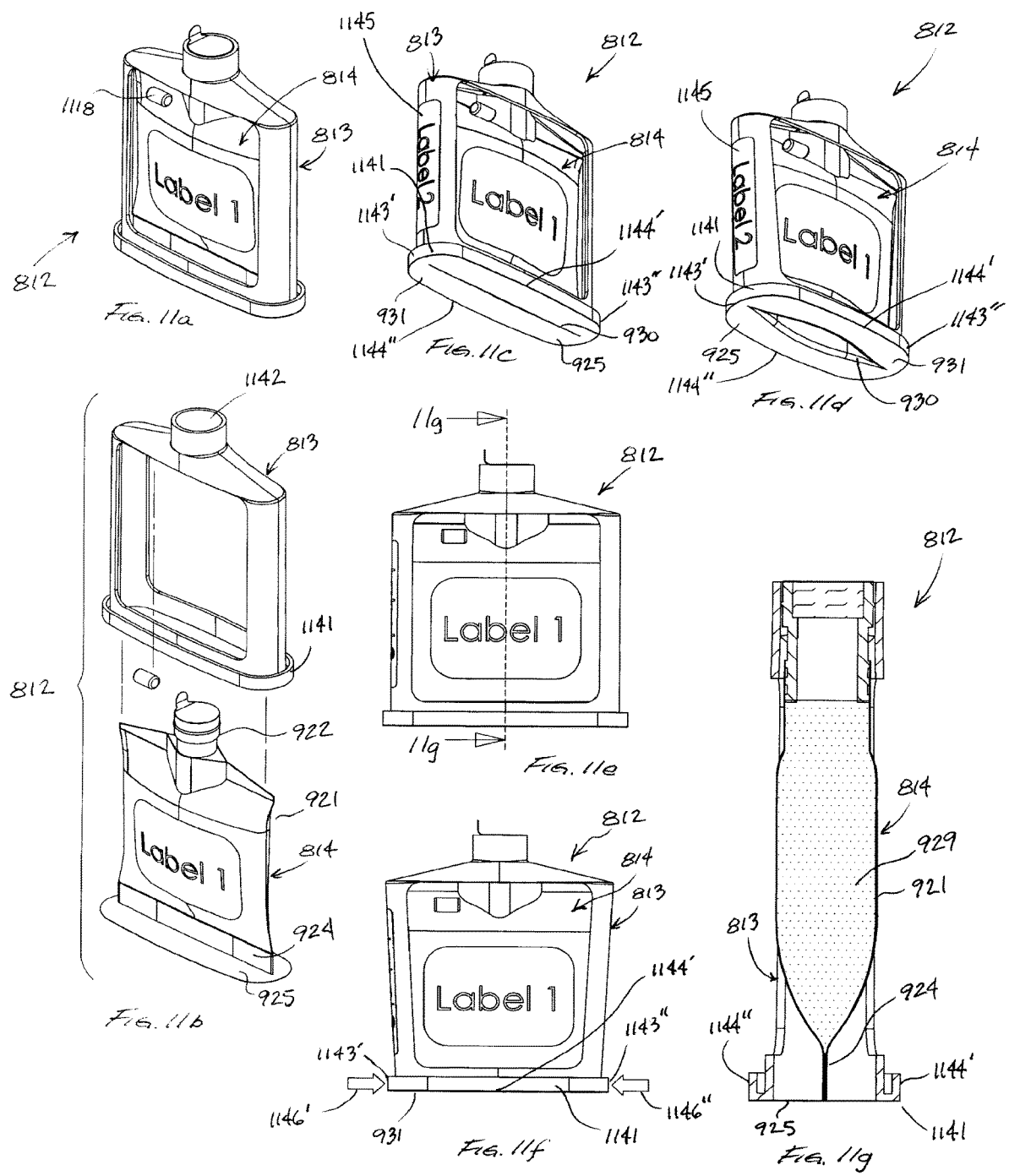

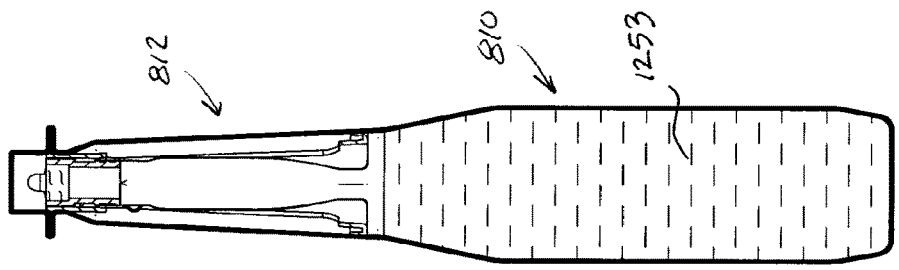
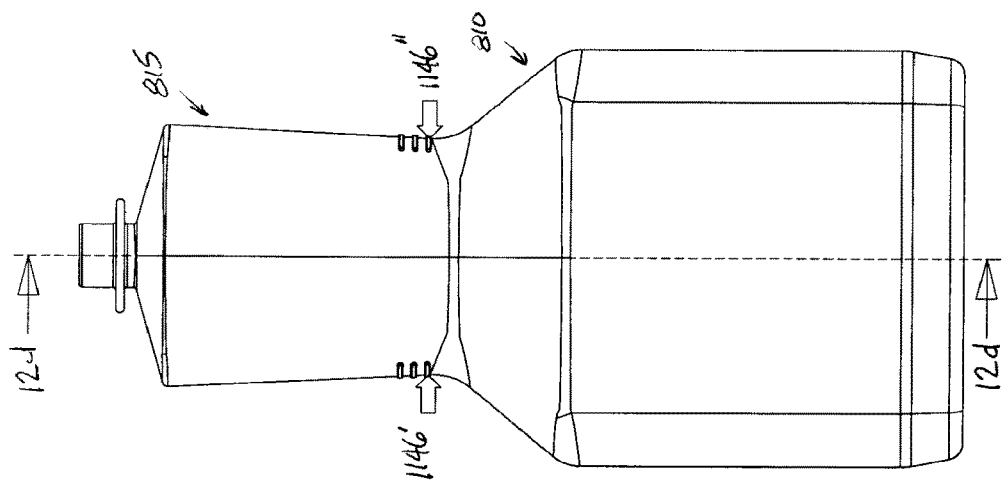
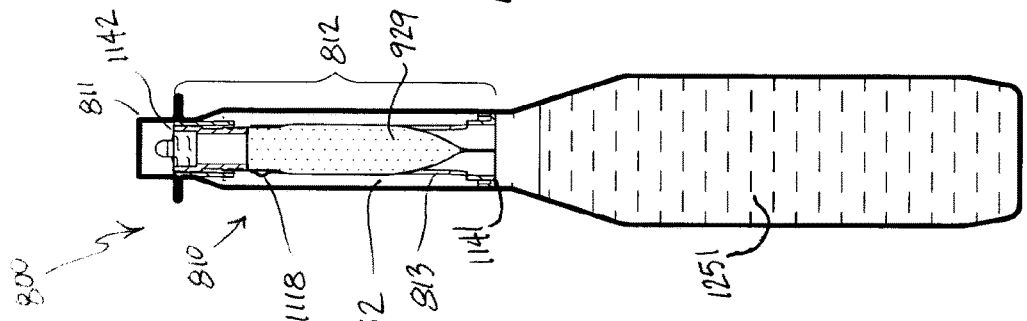
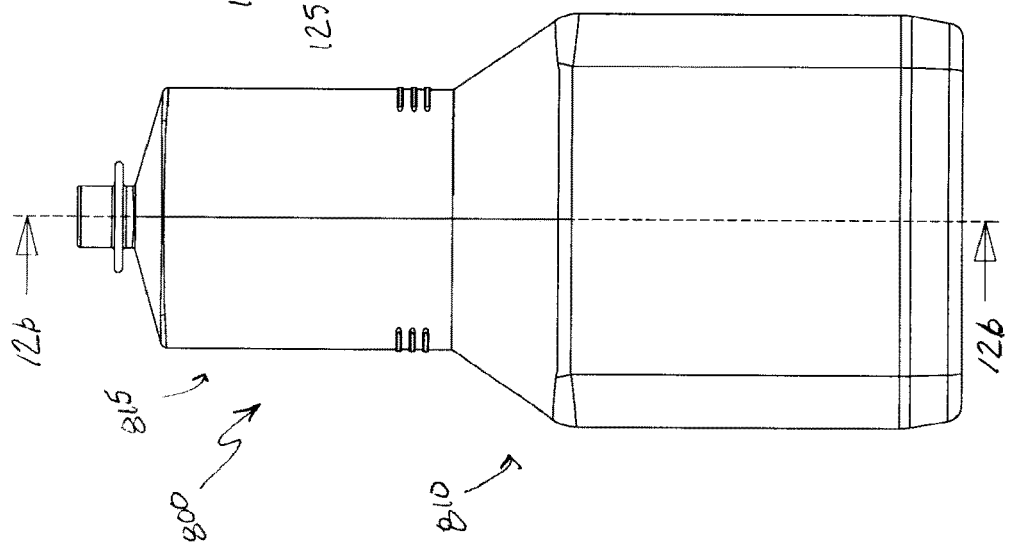

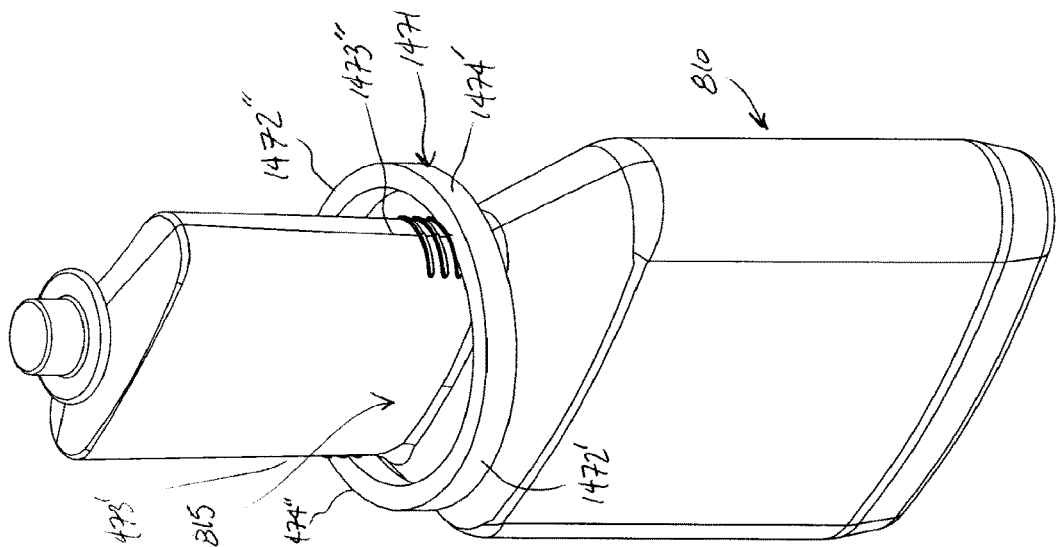
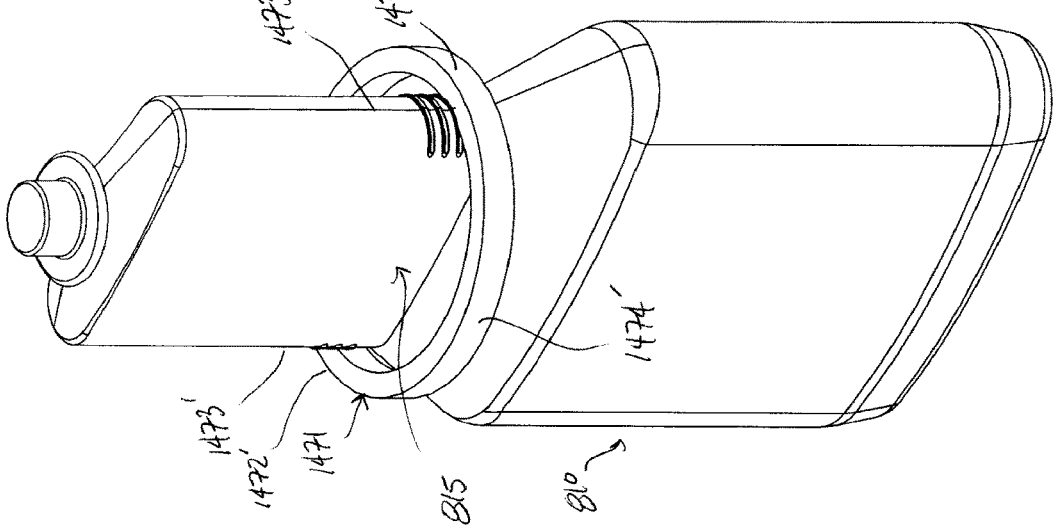
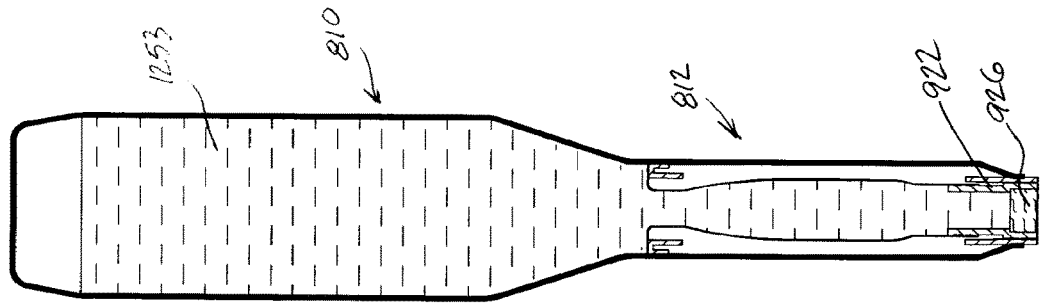

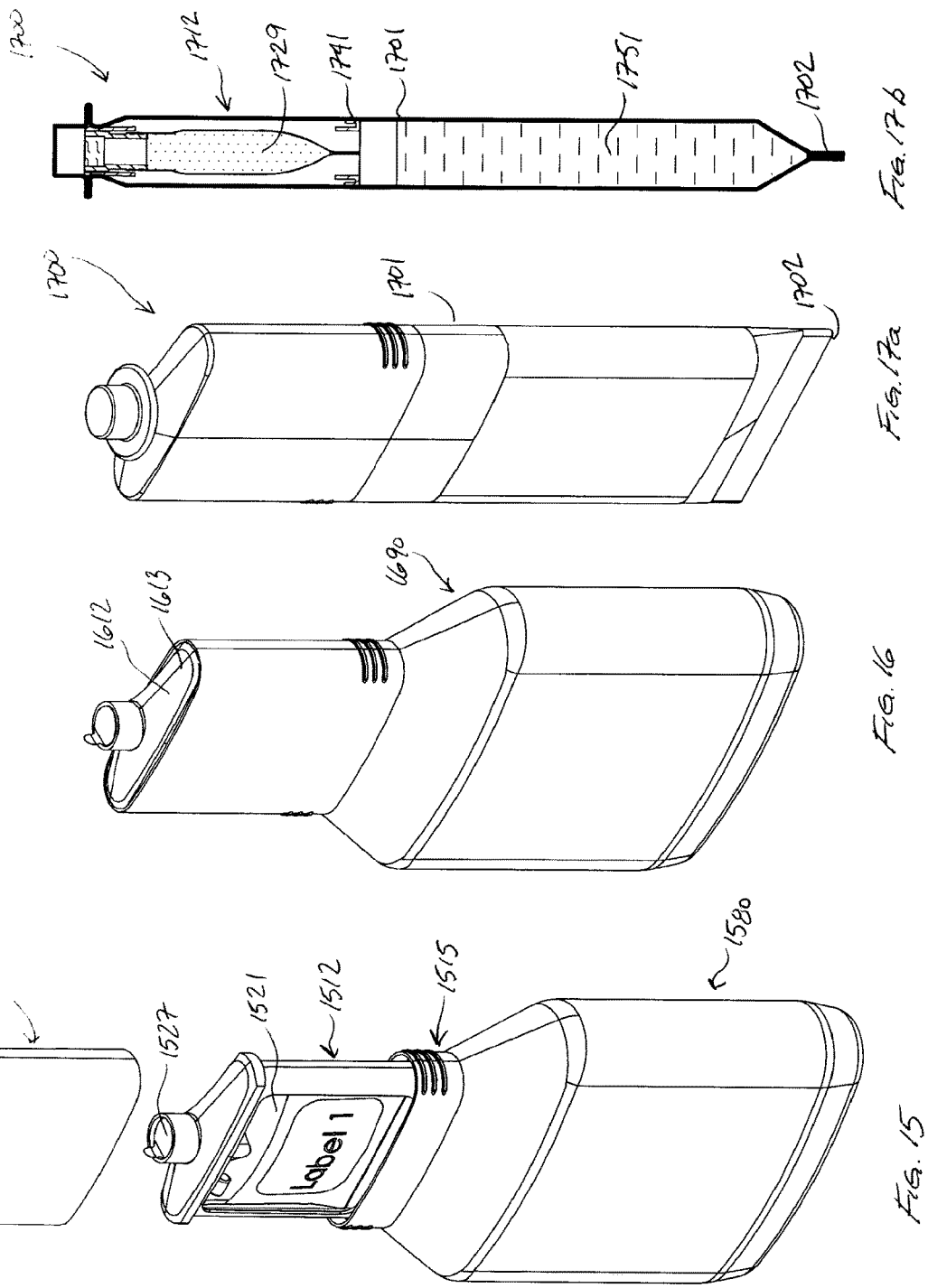

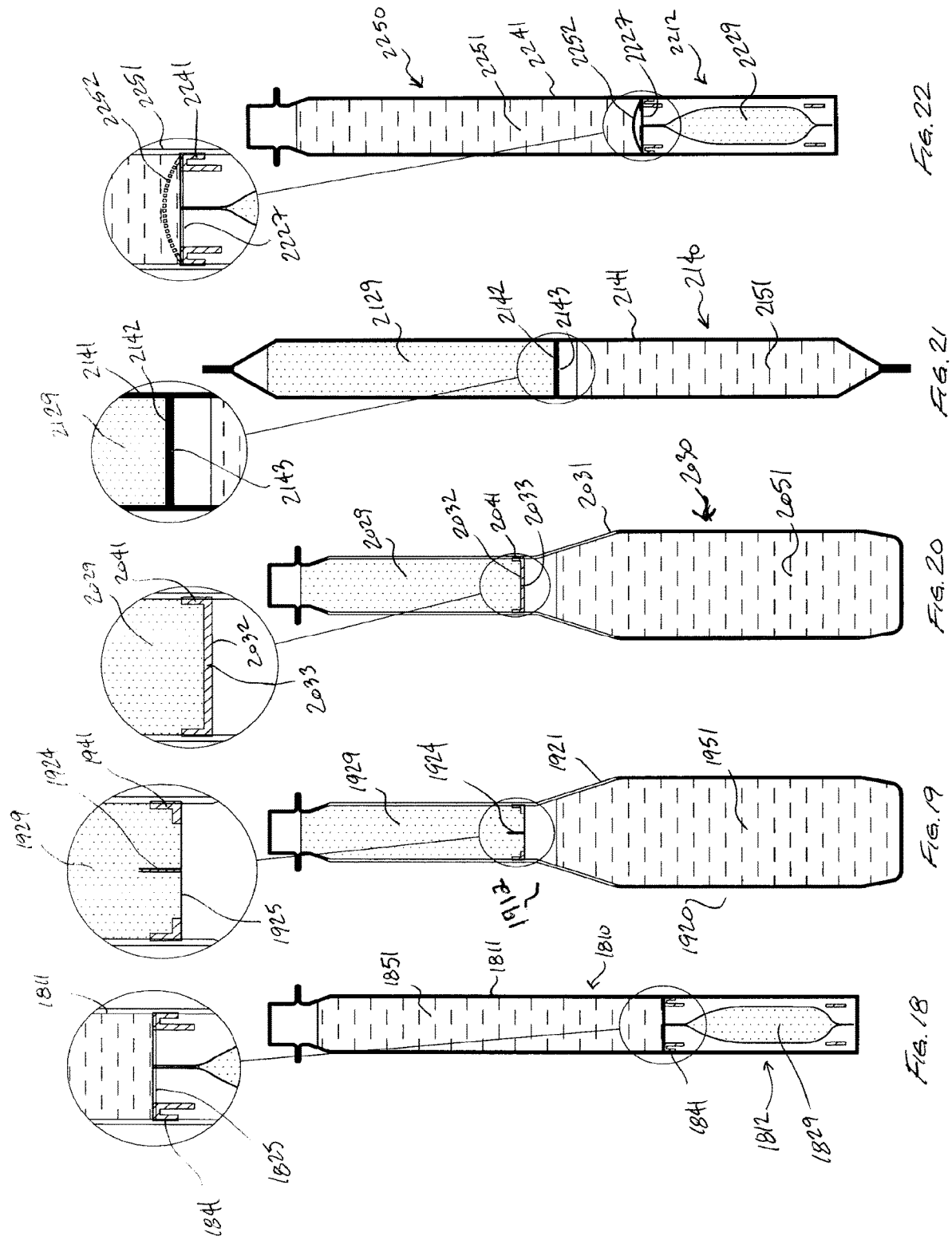

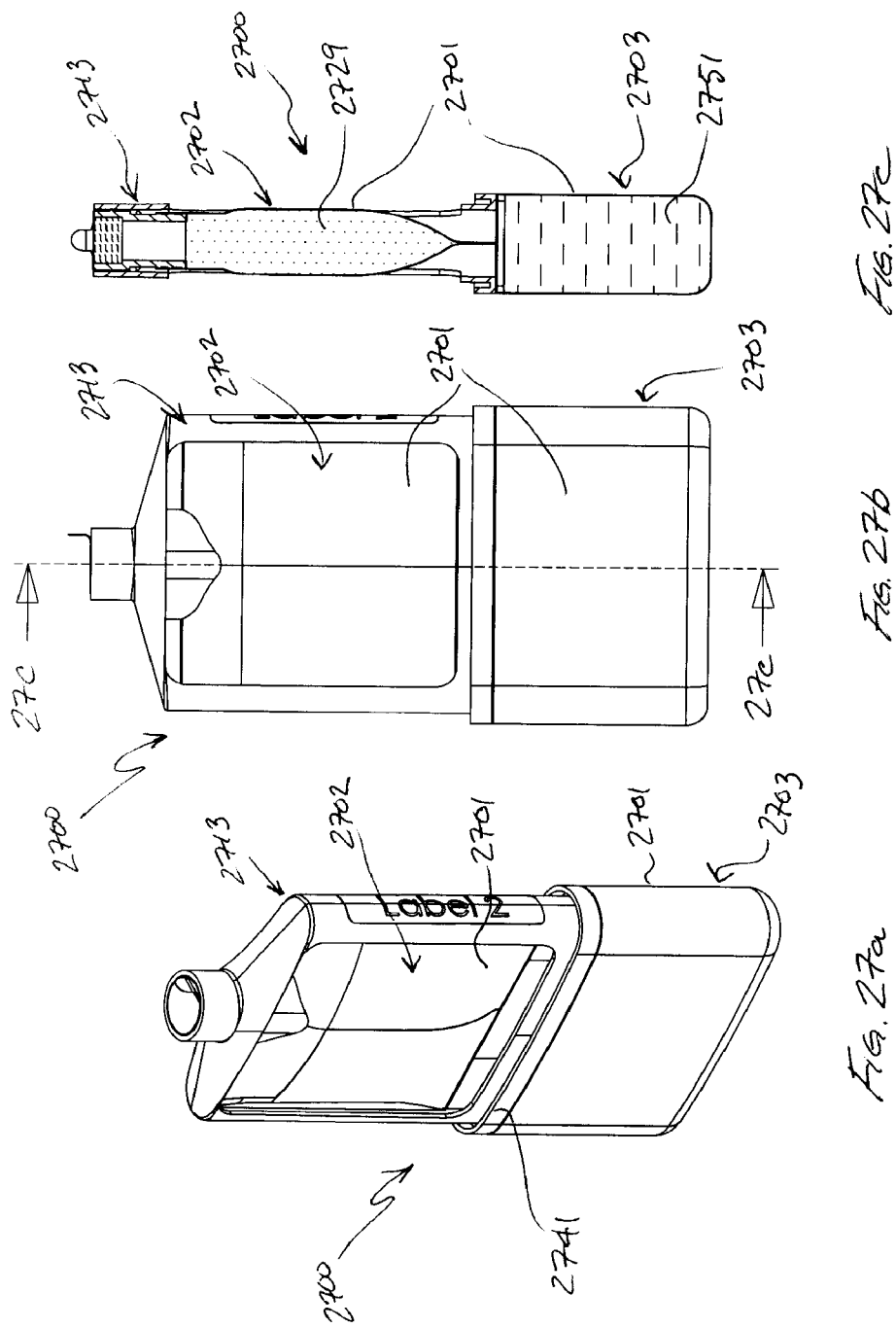

PACKAGED PRODUCTS, INSERTS AND COMPARTMENTS FOR ASEPTIC MIXING OF SUBSTANCES, ALONG WITH METHODS FOR USE THEREWITH

CROSS-REFERENCE TO RELATED APPLICATIONS

The present application claims the benefit of U.S. Application Ser. No. 61/143,971 filed on Jan. 12, 2009. The present application also claims the benefit of U.S. Application Ser. No. 61/261,315 filed on Nov. 14, 2009. The disclosures of each of the above applications are incorporated herein by reference in their entireties for all purposes.

FIELD

The present invention relates generally to packages with mixing capability of more than one substance, and more particularly to aseptic packages with aseptic mixing capability.

BACKGROUND

Aseptic prefilled packages are commercially available and commonly used in the medical, cosmetic and food industries as well as in applications outside of this field. Aseptic packages provide a hermetic barrier between the product contained therein and the exterior of the package to minimize or avoid environmental exposure, exposure to contaminants, and permeation of gasses and moisture.

In various applications it is desired to deliver the contents of the aseptic package outside of the package and such packages will be equipped with a fluid transport device for such purpose. Also, in some applications it is desired that the aseptic package will function as a dispenser of the contents therein, and to do so the aseptic dispensing package is equipped with a fluid transport device in the form of an exit port furnished with the applicable applicator such as a nozzle, spout, dropper, spray-head, topical applicator, ocular or ear applicator cannula, needle, micro-needles, or an adaptor (including connector, fitting, tube, hose or sealing member) to connect to the desired applicator or device. In a common arrangement the applicator is confined with in the aseptic package such that it is exposed to the product contained in the package but protected from the surroundings by the same barrier and to the similar extent as the product. The applicator is commonly either an integral feature of the package formed in the process of making the container, or inserted into the package either during the process of forming the package, before filling the package, or after filling the package. Aseptic packages are further commonly equipped with means for breaking the integrity of the aseptic package to expose the applicator, preferably without getting the applicator contaminated by the user hands or the exterior side of the package. A number of manufacturing methods have been developed over the year to form, fill and seal the package on a single piece of equipment.

Examples of aseptic dispensing packages include BottlePak® aseptic container products line by Rommelag® from Waiblingen, Germany. BottlePak®) utilize a blow-fill-seal process to form fill and seal a package in a single machine in aseptic conditions (hereafter some times referred to as "BFS" process). BFS method generally comprise the following steps: a) Extruding—a plastic parison, extruded from polymer, is accepted by the opened blow mold and cut below the die of the parison head, b) Molding—the main mold closes and simultaneously seals the bottom. The special mandrel unit settles onto the neck area and forms the parison into a container using compressed air or vacuum, c) Filling—by the way of the special mandrel unit, the product precisely measured by the dosing unit is filled into the container, d) Sealing—after the special mandrel unit retracts, the head muld closes and forms the required seal by vacuum, e) Mold Opening—with the opening of the blow mold, the containers exits from the machine and the cycle repeats itself. BottlePak® containers are sometimes equipped with a twist off portion that, when twisted off, expose an applicator which was integrally formed with the package. Such BottlePak® products include single dose eye drops ampoules with a pointy dropper tip or small parenteral containers with Luer-Lock connector (see more at http://www.rommelag.com/en05_applications/05_other_pharmaceutical.html). Some BottlePak® products comprise an insert which is inserted into the package post-filling and prior to sealing in proximity to the twist-off feature, such that upon twist off of the breakable portion of the package, the insert is exposed and facilitates the dispensing of the product contained in the package (here after "Blow-Fill-insert-Seal" process or "BFIS"). Examples of such products include an approximately 3 ml bellows-structure squeezable container comprising a stainless steel canula insert for hypodermic administration. Another example of BottlePak® BFIS product is a 1 Litter infusion bottle comprising a rubber septum to which an infusion set can be connected via a spike. The above manufacturing method is taught by U.S. Pat. Nos. 7,192,549, 7,004,213, 5,836,922, 5,687,550.

Similar BFS and BFIS products to the BottlePak® products are available from Weller® (Elgin, Ill.) http://www.weiler-bfs.com/asep-tech_systems/applications.html.

Further aseptic packages similar in form and function to BFS and BFIS unit dose containers are manufactured by Form-Fill-Seal process ("FFS") and are available from Sarong, Italy (www.sarong.it) and Unifil from Villafranca Di Medolla, Italy (www.unifil.it). FFS method forms the individual packages from continuous film strips which are thermoformed, partly sealed, filled, and then sealed on a single piece of equipment. An insert can be introduced to the package after the forming step and prior to the sealing step (pre or post filling) or after sealing the package.

Similar aseptic packages are manufactured by injection molding of a strip of several packages or individual packages which are filled from the back side (i.e. not the dispensing side) and sealed in subsequent steps. An insert can be incorporated in the package during or post the injection molding step. Such packages and equipment for making such packages are available from Lameplast® Rovereto di Novi, Italy (www.lameplast.it), and Sanner Plastic Technology from Bensheim, Germany (www.sanner.de).

If sterility of the product is desired it can be achieved by either performing the production in aseptic and sterile conditions using pre-sterilized raw-materials, components and substances, or by sterilizing the product after production or after a certain production step, or by a combination of the above approaches.

In some applications it is desired that an aseptic package will Include more than one substance compartment such that the plurality of compartments could be mixed to form a product prior to dispensing. In non-aseptic applications several methods could be applied to open a number of compartments or separate packages and to introduce the content of one package or compartment to another to formulate a product. For example hair-dye products such as Just-For-Men from www.justformen.com come in a retail package containing two bottles where the contents of said packages need to be mixed prior to application. One of said bottles comprise enough free space to receive the content of the second package such that the procedure of preparing the product is a) to remove the closures from both bottles, b) pour the content of the smaller bottle into the larger bottle, c) agitate, and dispense. While the method is practical, simple and does not require any dedicated package design or additional equipment, such a method will not be acceptable for applications where aseptic conditions are to be maintained until and during application (dispensing).

Several patents disclose caps for mixing a substance stored in the cap with the content of the container to which said cap is mounted. U.S. Pat. No. 7,464,811 teaches a mixing cap comprising an apertured inner tube threadably-engagable to the mouth of a bottle, and an outer housing cooperatively-engaged to the inner tube and slidably-restricted thereover via a flange arrangement. Preloaded ingredients contained within the outer housing may be introduced or discharged into the bottle by simply depressing the outer housing over the inner tube, thereby permitting the ingredients to flow through the apertures of the inner tube and into the liquid contents of the bottle. The combined ingredients and liquid within the bottle may subsequently be shaken without fear or risk of leakage or spillage. This mixing solution as well as many of the mixing caps known in the art suffer from two main disadvantages: a) the substance in the cap is not guarded at the same level of isolation from the environment as the product in the container, and b) in the procedure of merging the contents of the cap and the container the aseptic integrity of the package in breached (in the case of U.S. Pat. No. 7,464,811 the slideable part of the cap slides down to include an external portion of the cap in the sealed product space.

Various solutions have been developed for aseptically mixing the products of two compartments of a package. One advantage of such packages is that they provide longer shelf life and/or are more tolerable to storage conditions where the combination of the products of the two compartments suffer from accelerated deterioration or is sensitive to conditions such as temperature or exposure to light, or to avoid interaction between a substance in the first compartment with a substance in the second compartment. In other applications the products of the two compartments react as a desired step of the application and must be maintained separately such that the reaction occurs only before, during or immediately after the application (dispensing).

U.S. Pat. No. 7,025,200 to Fontana discloses a bottle for two-component extemporaneous products, of the type that comprises: a container for a first component, which is provided with an upper mouth; a reservoir for containing a second component, which is inserted substantially coaxially in the mouth, is open upward and has a bottom constituted by a diaphragm; a perforator, which can be inserted in the reservoir and is adapted to pierce the diaphragm in order to mix the two components; and a removable cap for closing the container in an upward region; the cap comprises a lower annular portion that is fixed to the container and an upper cylindrical portion that cooperates with the perforator and is rigidly coupled to the annular portion at an intermediate weakened region suitable to act as sealing means, a downward pressure on the cylindrical portion being adapted to disengage it from the annular portion and to make the perforator slide in the reservoir in order to pierce the underlying diaphragm. Various alternative approaches are disclosed in prior art including U.S. Pat. Nos. 3,968,872, 5,029,718, 5,543,097, 5,884,759, 6,148,996, 6,435,341 differing to some extent by the mechanism details, steps, and actions needed to cause two compartments to mix. The inventor of the current invention believes that those prior art approaches suffer from some common drawbacks:

a) Seal Quality—the seal between the first compartment and the second compartment, and the seal between at least one of the compartments and the environment is achieved either by press-fit or through at least portions by thin molded plastic wall. As used herein, the term press-fit seal in this patent refers to a seal caused by forcing two semi elastic components against each other such that a deformation is caused to a circumferential contact line between said two components to prevent migration of substance through this contact line. A surface stress remains along this contact line due to the elasticity of the components that maintain the seal even if reasonable pressure or force is biasing against that function of the seal. The term molded plastic component refers to components manufactured by either injection molding or blow molding or similar methods or by methods incorporating one of those methods. The wall of molded components have limited moisture barrier properties and therefore where the product in the one compartment is water or a solution and the product in the other compartment is super-dry powder or solid in other forms which needs to maintain in super dry conditions, molded components can not provide the required barrier for an extended time. The same drawback exists with press fit seals.

b) Another disadvantage of the prior art is that it can not support aseptic delivery (i.e dispensing, application, administration, etc). Because these packages are designed to be aerated as the content is expelled. Alternatively, though not proposed by their inventors, the packages in the prior art could be squeezed to cause the content to expel without air penetrating the package. The drawback there is that the arrangements in those different approaches would not allow an efficient expression rate of the content since those arrangements occupy or stiffen a substantial portion of the package that could not be squeezed.

The drawbacks listed above are partly overcome by U.S. Pat. Nos. 6,203,535, 5,176,634 and 6,996,951, 4,602,910, 5,462,526, 5,287,961, 4,961,495, 4,608,043, 5,425,447, 3,749,620, 6,017,598, 3,074,544, 3,608,709, 3,847,279, all of which disclose a film package comprising at least a first and a second compartment separated from each other by a frangible seal (some times referred to as peelable seal) such that under the presence of pressure in at least one of said two compartments the frangible seal separates causing the content of the two compartments to mix. In particular Smith's U.S. Pat. No. 5,176,634 teaches a flexible container is provided for the storage and mixing together of diluents and medicaments. The container incorporates multiple compartments, separated by frangible seals, in which the diluents and medicaments are stored. The seals are ruptured by manipulation of the container to thereby mix the contents together for delivery through a standard IV arrangement to a patient. The express ratio of such packages is high as there is not much resistance or obstacles to prevent the package from efficiently collapsing. The seal is formed by a weld between two walls of said film package with substantial weld-width resulting in good moisture barrier properties. While these approaches overcome some of the drawback of the prior art they lack the ergonomic properties that the rigid containers of the first group of prior art listed above. For several applications flexible packages do not meet the common form of presentation, for example in the field of infusion containers the European Market is customary to semi rigid bottles rather than the infusion bags which are more common in other parts of the world.

US Patent Application Publication No. 20060276755 teaches a valved medicament delivery device including a housing having a chamber including coaxially aligned inlet and outlet, a medicament cartridge located within the chamber having a passage therethrough and membranes sealing the passage having a burst pressure of less than 10 atmospheres, a manually actuatable fluid delivery device having an outlet in fluid communication with the chamber and a manually actuated valve located between the outlet of the fluid delivery device and the chamber inlet for delivery of fluid under pressure to the valve. The medicament delivery device of this invention may be utilized to deliver a controlled unit dose of a medicament on demand by first pressurizing a pressure chamber in the pressure delivery device upstream of the valve, then opening the valve to open the membranes and express the medicament through the chamber outlet. In this patent the second compartment with the second substance is external to the syringe with the first substance thus the mixing of the two compartments occurs when the environment is no longer inherently aseptic. In addition this patent teaches a method of first mixing the first substance and the second substance but instead the dispensing occurs simultaneously with mixing.

It is therefore an intention of the present application to provide a multi-compartment chamber which can provide high barrier properties between said compartments, have good expression rate, yet allow for the ergonomics of a molded package and could be manufactured in a method that reduces contamination risks.

SUMMARY

A packaged product is provided and comprises at least one container storing a first substance and a substance insert storing a second substance that is at least partially stored within the container. At least a portion of the substance insert comprises a flexible barrier between the substances. When integrity of the flexible barrier is jeopardized by external aseptic manipulation of the packaged product, the first and second substances are allowed to merge.

In some arrangements, the substance insert comprises a frame which may be rigid or semi-rigid. The frame may be a deformable member which supports a susceptible portion of the flexible barrier to translate deformation of the container into a resulting force on the flexible barrier, or to translate pressure applied to the flexible barrier into an applied force on the susceptible portion. In some arrangements, deformation of the frame translates into movement of the second compartment which damages the flexible barrier, such as breaking its seal or rupturing it, to permit the first and second substances to merge.

The substance insert is partially or entirely disposed within the container, and one or more such inserts may be provided. During manipulation of the packaged product, at least a portion of the substance insert may move to reduce the volume of the second compartment. In some arrangements, the substance insert comprises a pouch which contains the second substance. In other arrangements, a blister pack is provided. Still in other arrangements, the substance insert comprises a plunger assembly movably disposed within the container between a pre-activation position, wherein the first and second substances are separated by the flexible barrier, and an activation position, wherein integrity of the flexible barrier Is jeopardized to allow merger.

Preferably, an interface mechanically engages the substance insert with the container, for example, via a bond, a weld, a mechanical interlock or any combination thereof, to provide a fluid tight seal. The interface supports the flexible barrier to cause the integrity of an acceptable portion of the barrier to be jeopardized by pressure or movement of the substance insert. In various embodiments, the substance insert is engaged with the container via an interface that remains attached to the container in a fluid tight seal during customary use of the packaged product.

In an exemplary embodiment, the container comprises a first compartment for storing the first substance, and the substance insert comprises a second compartment for storing the second substance. Preferably, the second compartment also provides the flexible barrier. In some arrangements, a third compartment stores a third substance to be merged with one or both of the first and second substances. The third compartment may substantially encapsulate the second compartment to surround it with a desired environment. In some arrangements, the third compartment is separated from the first compartment by a substance insert interface.

The flexible barrier may be a film; a foil; a laminate; a multi-layer product combining films, foils and laminates; an injection molded portion; a blow molded portion; or any combination thereof. The barrier may be jeopardized in a variety of ways, such as breaking a frangible seal or through rupturing the barrier. This may be caused by movement of the substance insert or pressurization of one or more of the first and second substances. The flexible barrier is supported such that pressure or movement of the substance Insert jeopardizes a susceptible portion of the barrier.

In some arrangements, a fluid transport device (FTD) is provided for dispensing the merged contents of the container. The FTD may have a variety of configurations such as a topical applicator, a spray head, a squirt nozzle, a dropper nozzle, a nasal applicator, an oral applicator, an aural applicator, an invasive applicator, a connector, or any suitable combination thereof. The FTD, itself, may be an insert that is disposed entirely within the container and, in some arrangements, a removable guard aseptically protects the FTD from an ambient environment. The product may also comprise a FTD disabler from preventing continued use of the FTD, as appropriate or desired. In some arrangements, the substance insert and the FTD are a common insert. In some arrangements, the substance insert and the FTD are located proximately to, or distally from, one another. In some arrangements, at least a portion of the FTD is inserted into the container, while in other arrangements, at least a portion of the FTD is integrally formed in the container. In the various embodiments, the FTD allows for Introduction of a substance into either the container or the substance insert.

The container may assume a variety of configurations. In some embodiments, the container is configured generally in the shape of a bottle which comprises the first and second storage compartments and a neck portion. The substance insert may be accommodated partially or entirely within the neck portion. Preferably, the substance insert is supported relative to the neck portion such that deformation of the neck portion results in a corresponding deformation of the substance insert. A separate actuator may be employed to deform the neck portion in this regard. In the bottle configuration, as well as other configurations, the container may comprise an inlet FTD for receiving the first substance and an outlet FTD for dispensing the merged container contents.

The inlet and outlet FTDs may be the same. Other configurations provide a container in the form of a squeeze tube. The container may be formed by one of injection-molding, blow molding, blow-fill-sealing, blow-fill-insert-sealing, form-fill sealing, and injection-blow-molding, for example.

Arrangements are also provided for a substance insert for use in a packaged product that includes an integrally sealed container within which the insert is intended to be at least partially inserted. Broadly, the substance insert comprises (1) a compartment storing a substance; (2) a container interface for confronting a wall of the container, wherein the container interface comprises a first material; and (3) a flexible barrier comprising a second material different from the first material whereby sufficient external manipulation of the container will jeopardize the integrity of the flexible barrier without jeopardizing integrity of the container, thereby to allow the substance to be dispensed from the compartment. Another exemplary embodiment of a substance insert comprises (1) a compartment storing a substance; (2) a container interface for confronting a wall of the container; and (3) a flexible barrier supported by the container interface to deliver force, whereby sufficient external manipulation of said container will cause the container interface to affect force to the flexible barrier which will jeopardize an integrity of the flexible barrier.

The compartment for the substance Insert, the container interface, and the flexible barrier may assume one or more of the different arrangements and combinations discussed above. The substance Insert may also comprise a FTD and a frame, each as described above. In some arrangements, the first and second materials for the flexible barrier are integrated into a single part, and they may comprise layers of a multi-layer flexible barrier. In some arrangements, the first material is an adhesive.

Also provided is a substance compartment comprising a flange, and a drawn cavity having a proximal end which extends from the flange to a distal end. The distal end may accept a substance, while the proximal end is collapsible to form a frangible seal aseptically sealing the substance in the distal end of the cavity. The substance compartment may also comprise a FTD at least partially disposed in the distal end of the cavity.

Various methods are contemplated by the disclosure. One embodiment provides a method for use with a packaged product such as described above. According to this method, the container is externally and aseptically manipulated to jeopardize the integrity of the flexible barrier, thereby forming a merged compartment within the container to allow merger of the first and second substances. The method may also comprise dispensing the merged contents through a FTD that is moved, either rotationally or otherwise, from a pre-dispensing position wherein the FTD is separated from the merged compartment, into a dispensing position wherein the FTD is in communication with the merged compartment. In other arrangements, the FTD is disposed at least partially within the container and the packaged product is externally and aseptically manipulated by moving the substance insert away from or toward the FTD, or by moving the container relative to the FTD. During external manipulation of the container, which may occur either manually or through an actuator, at least a portion of the substance insert moves in correspondence with the container. In some arrangements, the first substance, the second substance, or both are pressed against the flexible barrier upon external manipulation of the container. Integrity of the flexible barrier may be jeopardized by movement of the product insert in response to deformation of the container. The barrier can be jeopardized by separating a frangible seal, rupturing the barrier, or otherwise.

A method is also contemplated for manufacturing a packaged product. According to this method, (1) a container of a selected configuration is formed that comprises at least a first compartment for storing a first substance; (2) a substance insert is formed which comprises a second compartment filled with a second substance; and (3) the substance insert is inserted at least partially into the container such that a flexible and susceptible barrier is interposed between the first and second compartments. In this context, susceptibility of the barrier is intended to mean that its integrity can be jeopardized in any of a variety of manners, such as by breaking a seal, rupturing the barrier, puncturing the barrier, or otherwise. In some arrangements, the substance insert is formed to include a pouch with a FTD on one portion of the insert and a frangible seal on another portion of the insert. The pouch may be supported in a deformable or rigid frame. In another arrangement, the substance insert is formed as a blister pack.

Some embodiments provide a plurality of at least partially collapsible substance inserts, each comprising a respective compartment that is filled with a respective substance, with each of the substance inserts being inserted at least partially into the container. The first compartment may be interposed between the substance inserts. In other embodiments, the container includes a plurality of container compartments, each storing a respective substance, and the substance insert is interposed between the container compartments. Preferably, the container is at least partially deformable and may be configured as a squeeze tube, a bottle or any other suitable configuration.

According to this method, the first substance may be introduced into the first compartment either prior to or after insertion of the substance insert. The FTD may also be inserted into the container. The method may also incorporate a Blow-Fill-Insert-Seal (BFIS) process whereby (1) at least a portion of the container is blow molded to form the first compartment; (2) the first substance is introduced into the first compartment; (3) the substance insert is inserted into the container; (4) the first substance and the substance insert are aseptically sealed inside the container; and (5) the substance insert is interfaced with an interior of the container in a fluid tight manner. A FTD may be either inserted partly into the container or formed in the container. Also according to this method, the container may be molded, with the substance insert introduced at least partially into an opening of the container and interfaced in engagement with the container, preferably by sealing.

BRIEF DESCRIPTION OF THE DRAWINGS

FIGS. 3a-3d demonstrate another exemplary embodiment where the substance-insert is associated with the applicator-insert;

FIG. 3e illustrates a syringe which employs the packages shown in FIGS. 3a-3d;

FIGS. 5a-5h demonstrates a further preferred embodiment where the second compartment is a film pouch associated with the applicator insert.

FIGS. 11a-11g show views of an exemplary embodiment of the product-insert in the sealed and open states;

FIGS. 12a-12d show detailed views of an exemplary embodiment of the package in the sealed and opened states;

FIG. 13 shows the container of FIG. 8 in an in-use state;

FIGS. 14a-14b show an exemplary embodiment of the package where an external device facilitates the manipulation of the container to the open state;

FIG. 15 shows a further exemplary embodiment of the package where a removable section provides access to the fluid transport device and exposes a portion of the substance-insert;

FIG. 16 shows a further exemplary embodiment of the package where a portion of the substance-insert is exposed;

FIGS. 17a-17b show a further exemplary embodiment of the package where the container is in a form of a tube;

FIG. 18 shows an exemplary embodiment where the substance-insert is spaced apart distally from the fluid transport device;

FIG. 19 shows an exemplary embodiment where the substance-insert is reduced to a flange with a film valve;

FIG. 20 shows an exemplary embodiment where the substance-insert is reduced to a flange with an integral valve;

FIG. 21 shows an exemplary embodiment where the valve is integral to the container:

FIG. 22 shows an exemplary embodiment where the substance-insert comprises a filter;

FIGS. 27a-27c shows an exemplary embodiment where the web of the pouch of the second-compartment forms the first compartment.

DETAILED DESCRIPTION

Figure 1A:
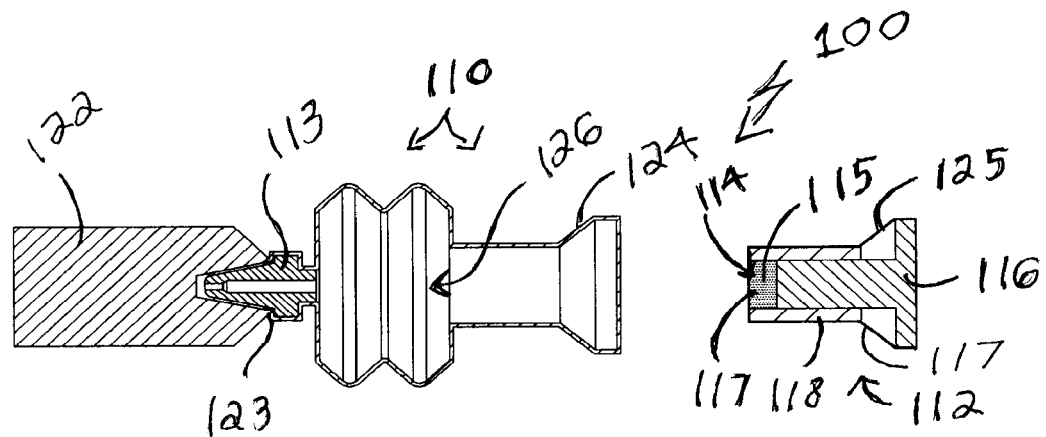
FIGS. 1a-1c demonstrate a first exemplary embodiment of a package where the substance-insert is separated from the applicator insert.

Disclosed is a package in the form of a container comprising a first compartment containing a first substance, and a substance-insert at least partly disposed in said container with said first substance. The substance-insert comprises a second compartment containing a second substance, and at least part of said compartment is made from flexible barrier wall. The package can be externally and aseptically manipulated to mix the said first substance and said second substance prior to dispensing, by jeopardizing the integrity of said film wall. The arrangement allows the container to be semi rigid thus providing better ergonomics of the package. The film wall provides a good barrier between the first substance and the second substance supporting longer shelf life and stability of the products.

The container can further comprise an insert comprising a fluid transport device. The fluid transport device can be in the form of an applicator for dispensing the content of the package in a desired fashion to a desired target. Various applicator types may be incorporated with the container to suit a designated application including a spout, orifice, tube, hose, dripper, brush, sponge, nozzle, spray-head, hypodermic needle, a micro needle or micro needle array, a needless injection orifice a canula a tube a combination of the above, or one or more of a connector, a passage, a facilitator, a valve, a septum or a coupler to one or more of the above applicators. The arrangement is such that when the integrity of the aseptically sealed container is broken at the designated location the applicator is exposed and becomes available for use.

In some embodiments the substance-insert and the applicator-insert are integrated as one insert, advantageously simplifying the manufacturing of the package. In other embodiments manipulation of the container to open also causes the first and second compartments to merge. In other embodiments the opening of the package is conditioned by first manipulating the compartments to mix. In yet other embodiments the merging of the compartments is conditioned by first manipulating the package to open.

The present invention is not limited to one substance-insert and is applicable to multi compartment-inserts. Furthermore the package may contain a plurality of first compartments that can be either utilized separately or merged.

The term dispensing generally refers to any form of expressing the content of the package and captures other terminology such as administration, delivering, infusing, dripping, application, pouring, smearing, spreading, injection and other forms of introducing a product to a target location in a desired fashion.

The term flexible barrier and the term film generally refers to mono-layer films, multi-layer films, extruded films, blown films, rolled films, laminated films, metal foils, ceramic or oxide laminates, blow molded, injection molded, cast, other forms of flexible barriers known in the art or combination of the above.

In some preferred embodiments the second compartment is at least partly made of film or foil and the integrity of the seal of the compartment is jeopardized (some times hereafter referred to as breached or opened) by either: a) separating or peeling apart a frangible seal between at least two wall of the second compartment, b) piercing at least one wall of the second compartment by a piercing object, c) or by breaking or rupturing at least one wall of the second compartment.

In some preferred embodiments the second compartment is completely made from high barrier film, advantageously providing a high barrier to moisture and gas.

The second compartment is manipulated to open and establish fluid communication with the first compartment by external manipulation of the package in an aseptic fashion.

In some embodiments said second substance comprises a liquid, a solution, a gel, paste, compressed powder, loose powder, a solid or solid particles, pellets, a lyophilized cake, emulsion, gas, or combination of the above. In some embodiments the second substance is a vaccine in a dry format and the first substance is a diluent and where said vaccine has improved stability and extended shelf life when in dry format, and where said diluent and dry powder vaccine are mixed to reconstitute prior to administration.

Administration can be in one of the forms commonly used in the art such as injection, topically, orally, nasally, by inhalation or by any other means known in the art.

In some embodiments at least one of the first substance and the second is pressurized by external manipulation of the container to cause the flexible barrier to be jeopardized to allow the first and second substances to merge. The flexible barrier is supported around its susceptible portion such that applied pressure to the flexible barrier is translated into applied force to the susceptible portion of the flexible barrier.

In some embodiments the interface of the substance insert with the container is such that deformation of the container will translate into movement of the substance insert. The interface supports the flexible barrier such that movement results in applied force to the susceptible portion of the flexible barrier. Thus external deformation of the container results in jeopardizing the flexible barrier allowing the first and the second substances to merge.

In some embodiments the package is made in a BFIS process. In other embodiments the package is made in a FFS method. In some embodiments the first compartment (or compartments) is blow molded or injection molded and the substance-insert (s) is introduced to the package prior, during or post molding of the first compartment, or during or post forming of the first compartment.

The term substance is generally referred to a content of a filled compartment prior to allowing it to merge with the other compartment or compartments which form a product. A substance may be a pure or uniform substance or a combination of substances.

In the following detailed description, reference is made to the accompanying drawings which form a part hereof, and in which is shown by way of illustrations specific embodiments for practicing the invention. The leading digit(s) of the reference numbers in the figures usually correlate to the figure number, with the exception that identical or common components which appear in multiple figures may at times be identified by the same reference numbers. The embodiments illustrated by the figures are described in sufficient detail to enable those skilled in the art to practice the invention, and it is to be understood that other embodiments may be utilized and changes may be made without departing from the spirit and scope of the present invention. The following detailed description is, therefore, not to be taken in a limiting sense, and the scope of the present invention is defined only by the appended claims.

In the description of the Figures the term front of a part, feature or an assembly refers to the side facing the application (or dispensing) end, and the term back of a part, assembly or feature is the side extending away from the application side.

Figure 1B:
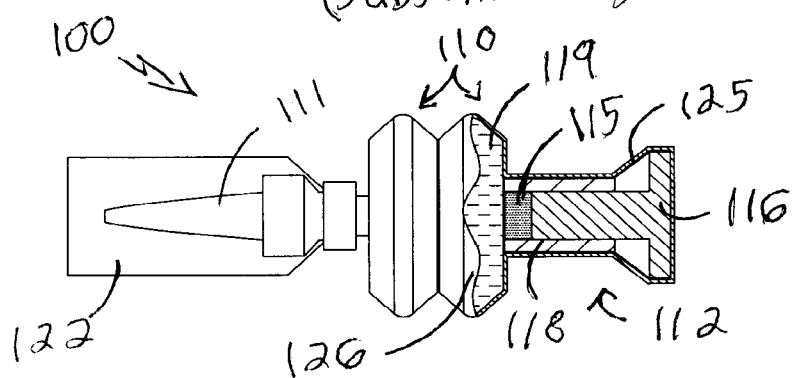
Figure 1C:
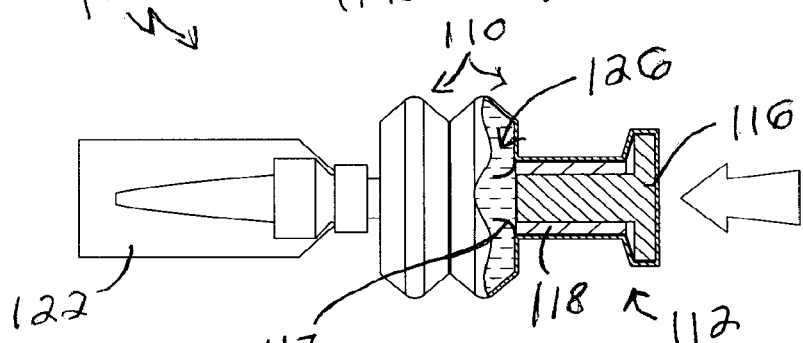

Referring first to FIGS. 1a-1c, a packaged product 100 is shown. Associated with package 100 is a container 110, in which a fluid transport device insert in a form of an applicator (here after sometimes referred to as "applicator-insert") 113, and a substance-insert 112 are separately Included in fluid communication with a first compartment 119 which is formed in said container. FIG. 1a shows an exploded side section view of the package 100 where the substance-insert 112 is offset from its actual position in the container 110. The applicator-insert 113 is in the fashion of a dropper nozzle, and is aseptically protected from the environment by a twist-off portion 122 integrally formed in the container 110. The twist-off portion 122 is connected to the container 110 via a weakened section 123 which will break upon a sufficient twisting action to expose the tip of the dropper nozzle 111 of the applicator-insert 113. The package of FIG. 1 can be manufactured by a BFIS method. With slight design modifications similar packagings could also be manufactured by a process involving injection-insert-molding or by a process involving blow molding, or by a FFS process. Where the manufacturing method is BFS or BFIS the applicator insert can be replaced by a similar feature directly formed in the container 110. Where the container 110 is manufactured by injection molding, the applicator-insert 113 can be replaced with a similar feature directly formed in the container 110, and the twist off portion 122 can be connected to the container 110 by ultra-sonic welding or spin-welding or any applicable connection method known in the art. The substance-insert 112 can be manufactured on a separate filling line. The applicator insert 113 can be one or more of a variety of fluid transport devices known in the art including, a topical applicator such as a brush, sponge, spatula or wiper; a spray-head, squirt-nozzle, a nasal applicator, oral applicator, or ear applicator; an invasive applicator such as a needle, a cannula, a soft cannula, a catheter, a tube or a hose; a connector such as a Luer Lock connector, a septum for receiving a needle or a hollow spike such as infusion set spike; other-applicators known in the art; or a coupler to one or more of the above. The container 110 can be manufactured from various materials known in the art including Polypropylene or Polyethylene.

The substance-insert 112 comprises a cylindrical barrel 118 in which a plunger 116 is disposed from the back end of said barrel 118. A flexible barrier in the form of a film portion 117 seals over the front end of the barrel 118, defining a second compartment 114 in the barrel 118 between said film 117 and the front end of the plunger 116. The second compartment is filled with a second substance 115. The second substance 115 can be in various forms including a liquid, emulsion, mixture, suspension, solution, gel, paste, solid such as compressed powder, loose powder such as spray dried or grinded powder, lyophilized cake, granulated substance, pellets, pill, gas, or any other form known in the art or a combination of the above. The film portion 117 extends to wrap around the barrel 118 and connect to the back end of the plunger 116 such that the isolation of the second substance from the environment does not depend on the seal quality of the cylindrical mating between the plunger 116 and the barrel 118. In other embodiments the flexible barrier 117 further extends to completely seal around the plunger 116 thereby establishing an integral film package around the substance-insert 112 which improves the barrier properties around the second substance 115. In another embodiment the film portion 117 is limited to the front end of the barrel 118 which provides a tight seal to the front side of the second-compartment 114, and the seal of the back end of the second compartment is left to the seal between the plunger 116 and the barrel 118 such as a tight-fit seal. In reference to the flexible barrier 117 the term film generally refers to films and foils including monolayer films, multi-layer films, extruded films, blown-films, laminated films, metal foils, ceramic or oxide laminates, other types of membrane materials or any combination of the above. The flexible barrier 117 can be attached to the rest of the substance-insert 112 by various means including heat seal such (heat stake, hot-plate, ultrasonic, RF, IR) or by adhesion or by any other means known in the art. The film portion 117 comprise a collapsible section 125 that interconnects (bridges between) the back end of the barrel 118 and the back end of the plunger 116, allowing relative motion of the plunger 116 into the barrel 118.

Referring now to FIG. 1b, a side view with a broken-out section of the package 100 prior to activation is demonstrated. The substance-insert 112 is accommodated in an extension of the first compartment 126 such that the product 112 is aseptically confined in the container 110; the film portion 117 separates between the first substance 119 in the first compartment 126 and the second substance 115 in the second compartment 114. The extension of the first compartment 126 comprises a collapsible portion 124 with a wall geometry similar to the collapsible portion 125 of the film portion 117 of the substance-insert 112, providing the flexibility for manipulating the plunger 116 to move forward inside the barrel 118. The first substance 119 can be in various forms including a liquid, emulsion, mixture, suspension, solution, gel, paste, solid such as compressed powder, loose powder such as spray dried or grinded powder, lyophilized cake, granulated substance, pellets, pill, gas, or any other form known in the art or a combination of the above. The portion of the wall of the first compartment 126 that confines the first substance 119 comprises a geometry of a bellows which allows for efficient expression of the first substance 119 therein when the first compartment 126 is forced to collapse. The barrel 118 provides an interface to the container 110 which is undisturbed during ordinary operation of the container. The barrel further supports a susceptible portion of the flexible barrier 117.

Referring now to FIG. 1c the package 100 is demonstrated after activation. The plunger 116 is displaced forward by applying external force as the arrow indicates. Moving forward the plunger 116 causes the second substance 115 to press against the susceptible portion of the flexible barrier 117 in front of the barrel 118. As the susceptible portion of the flexible barrier 117 is supported by the barrel 118 the applied depression of the second substance 115 is translated to applied force on the susceptible portion causing it to rupture and establish fluid communication with the first substance 119, allowing the two substances to merge into a merged compartment. In another embodiment the extension of film portion 117 is limited to the front of the barrel 118 and the seal between the barrel 118 and the film portion 117 is such that pressing the content 115 causes the flexible barrier 117 to peel (rather than rupture) and thereby establish fluid communication with the first fluid 119. When the plunger 116 is fully pushed forward the head of the plunger 116 is flush with the front of the barrel 118 and the back wall of the first compartment 126. In further activation steps the twist-off portion 122 is removed, at which point a squeeze of the first compartment 126 by further application of force on the plunger 116 in the direction of the arrow will cause the merged contents to expel through the applicator 113 (not shown).

In a further configuration the plunger 116 comprises a rupturable member extending into the second compartment 114 and reaching proximately to the susceptible portion 117 such that, as soon as the plunger 116 begins traveling forward, the rupturing member will reach the film portion 117 and facilitate the rupturing of the film 117. The rupturing member may be merely a sharp spike extending from the plunger head.

In a further embodiment a rupturing member is movably disposed in the second compartment 114 along with the second substance 115 such that, as soon as the plunger 116 begins traveling forward, the rupturing member will rupture the susceptible portion of the flexible barrier 117.

In some embodiments the twist off portion 122 can be replaced to protect the applicator for further uses. Where the applicator-insert is a sharp object the twist off portion can be replaced to avoid accidental contact with the sharp.

The package 100 provides a high level of ergonomics and a good content express rate, while also providing isolation of the first substance 119 from the second substance 115 through the high barrier film portion 117.

It will be apparent to those skilled in the art that the packaged product 100, as well as other packaged products and packaging described or contemplated herein, can be packaged in a secondary package such as a shipping package, a pouch, a package that reduces or eliminated exposure to light or to other environmental effects, and so forth.

It will further be apparent to those skilled in the art that the package can be associated in a further device, an actuator or system which facilitates the use of the package, or in which the package and dispensing thereof is being utilized.

It will further be apparent to those skilled in the art that certain embodiments may comprise a plurality of packages or a plurality of elements of the package combined with common elements of the package container. For example in one embodiment two first compartments each associated with a substance-insert may communicate with a common applicator-insert.

Figure 2A:
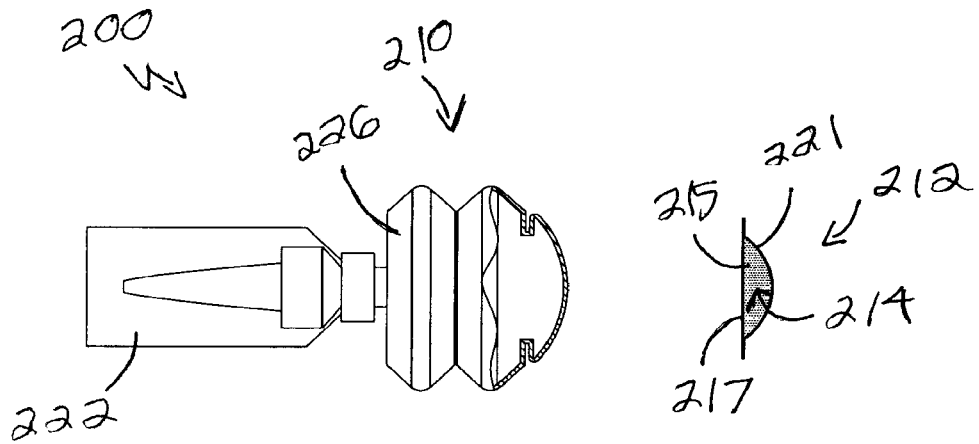
FIGS. 2a-2c demonstrate another exemplary embodiment of a package where the substance-insert is a blister.
Figure 2B:
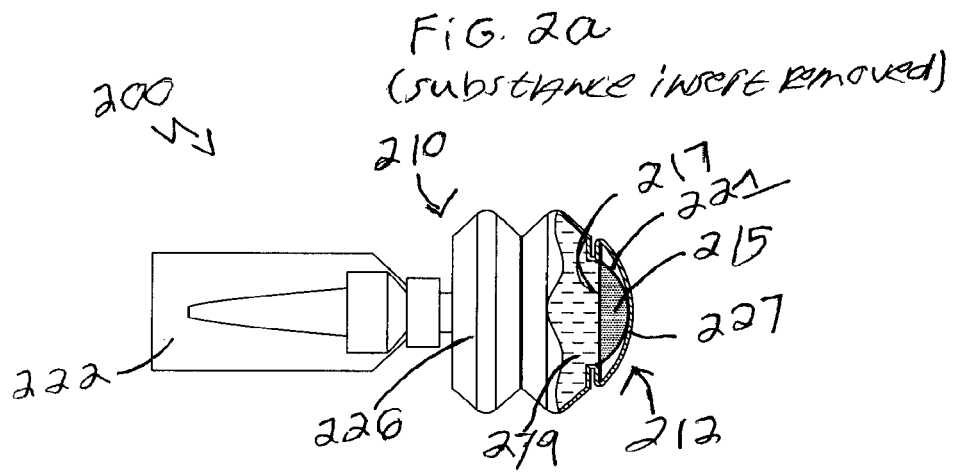
Figure 2C:
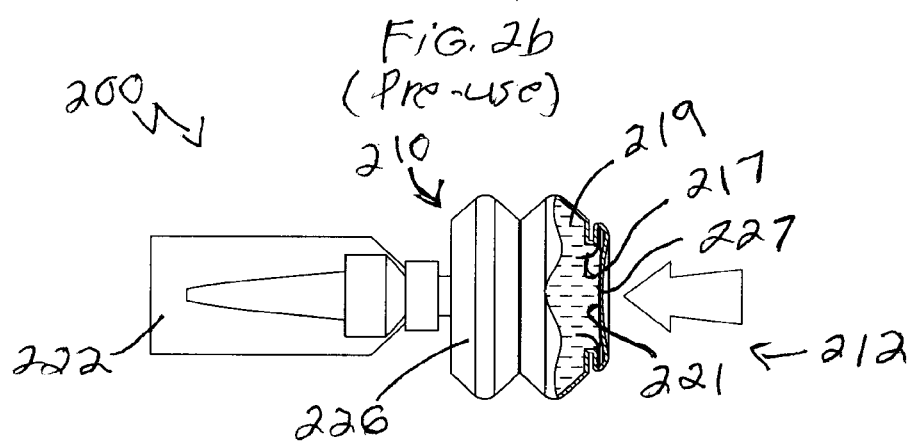

Referring now to FIGS. 2a-2c, a further exemplary package 200 is demonstrated. Like in package 100 of FIG. 1 the substance-insert 212 is accommodated in a backward extension of the first compartment 226. FIG. 2a demonstrates an exploded side view with a broken-out section where the product-insert 212 is offset backward from its actual location in the container 210. The insert 212 is constructed of a flexible barrier comprising a first film wall 217 and a second film wall 221 which is formed to have a concave shape. The two films are connected along their perimeters to form a sealed second compartment 214 in the form of a blister containing the second substance 215. The insert compartment can be manufactured in a FFS line or by any other manufacturing method known in the art and introduced to the container 210 during the formation of the container 210 or adjacent to the first substance (not shown) filling step. The joint perimeter of the blister defines an Interface to the container 210.

Referring now to FIG. 2b, The substance-insert 212 is accommodated in a pocket 229 at the back of the first compartment 226, such that the film wall 217 separates the first substance 219 from the second substance 215. The back wall 227 of the first compartment 226 has a dome shape that can be pressed to collapsed toward the substance-insert 212.

Referring now to FIG. 2c the package 200 is shown from a side view with a broken-out section, during the activation state. The back wall 227 has been manipulated to collapse into the first compartment 226 by applying force in the direction of the arrow, forcing the second wall 221 of the substance-insert 212 to also collapse into the second compartment 214, thereby causing the second substance 215 to press against the first film wall which is supported by the interface to the container. This translates the applied press of the second product on the first film wall 217 to applied force on the susceptible portion of the flexible barrier which causes it to rupture, allowing the first substance 215 and the second substance 219 to merge. Various mechanisms can facilitate the rupture of the first wall 217 of the substance-insert 212. In one embodiment the first film 217 comprise a slit line along its center that causes stress concentration as the second substance is pushing against first wall 217. The first wall 217 of the substance-insert 212 is shown ruptured whereby fluid communication is established between the first compartment 226 and the second compartment 214 allowing the first substance 219 and the second substance 215 to merge. Subsequent activation steps include removing the twist-off portion 222 thereby exposing the applicator (not shown), associating the applicator with its target, and continuing to press on the back of the first compartment to cause the product to expel through the applicator. The first compartment 226 has a bellows shape that allows for efficient express rationing of the content. The substance-insert 212 is mostly flat and flush with the back wall of the first compartment 226 such that it does not interfere with efficient expression of the content.

Referring now to FIGS. 3a-3e, a further preferred embodiment is demonstrated. FIG. 3a demonstrates a section view of package 300 at the pre-activation state. The substance insert 312 comprises a flexible barrier in a form of a film strip 333 which is folded over and sealed onto itself to form a second compartment 314 therein, leaving first and a second loose ends of the strip 334 and 335. The seal that forms compartment 314 is a frangible seal (sometimes referred to as peelable seal) that can be separated if the first and the second loose ends of the strip are pulled apart. The first end of the strip 333 is supported by the fluid transport device Insert 313 (also referred to as ("applicator-insert") in a form of an applicator, and the second end is supported by the plug 336. The applicator insert 313 comprises a needle assembly 331 comprising a needle 327 and a needle hub 329. The applicator-insert 313 further comprises a housing 332 in which the needle assembly 331 is accommodated such that it can be made to move backward along the longitudinal direction of the needle 331. The applicator-insert 312 further comprises a needle protector 337 having a proximal end attached to the housing 332 in an aseptically sealed fashion, and extending to provide a cover to the distal sharp end of the needle assembly 331. The plug 336 comprises a cylindrical engagement interface to the container which is connected in a fluid tight fashion to the back end of the container 310 and a grip portion extending backward from the seal portion to provide a convenient means for activating the package 300, as will be detailed bellow. The container 310 comprises a bellows having a front opening adapted to receive and engage with the housing 332 and a back opening adapted to receive the plug 336. The housing 332 of the applicator-insert 313 is accommodated in the front opening of the container 310 and sealed to it in a fluid-tight fashion. The plug 336 is accommodated in the back opening of the container 310 and sealed to it in a fluid tight fashion. The strip 333 and the second compartment 314 formed therein are confined in the first compartment 326 such that the seal of the strip 333 to itself constitutes a separation between the first substance 319 and the second substance 315.

Referring now to FIG. 3b, the package 300 is demonstrated during activation. The grip of the plug 336 has been pulled in the direction of the arrow thereby causing the first compartment to elongate. As a consequence the first end 334 of the strip 333 and the second end 335 of the strip are pulled apart causing the seal around the compartment 314 to separate, establishing fluid communication between the first compartment 326 and the second compartment 314 thereby merging the first and second substances into a merged compartment. In a further embodiment the arrangement is such that the plug is twisted or rotated relative to the housing 332, pulling the strip ends apart and separating the frangible seal of the second compartment 314.

FIG. 3c demonstrates the package 300 upon completion of the injection. The bellows is at the fully collapsed state leaving a minimal "dead-space" of unexpressed product. At this point the plug 336 mechanically engages the needle hub 329. The film strip 333 is flexible and thin enough so as not to present an obstacle for efficient expression of the contents of the container 310 when squeezed.

FIG. 3d shows the package 300 after the bellows has been restored substantially to its original shape. The plug 336 remains engaged with the needle hub 329 thereby pulling the needle assembly into the container 310 and disabling the package from being reused such that the tip of the needle is protected from causing injuries or damage.

FIG. 3e shows the package 300 accommodated in a device having a general form of a syringe 340 comprising a barrel 342, an actuator 344 and a spring 346 disposed therebetween biasing the actuator out of the barrel. The package 300 is supported by the front wall 348 of the barrel. In the back, the plug 336 is engaged with the actuator 344. The device 340 (which can also be considered a package) can ergonomically facilitate the operation of the package 300 and in particular the stage of reconstituting the original shape of the barrel in which the spring 346 will force the actuator 344 ouy of the barrel 342 and pull the plug along with it. The device can be part of a single use kit along with the package or can be used multiple times by replacing the package 300.

Figure 4A:
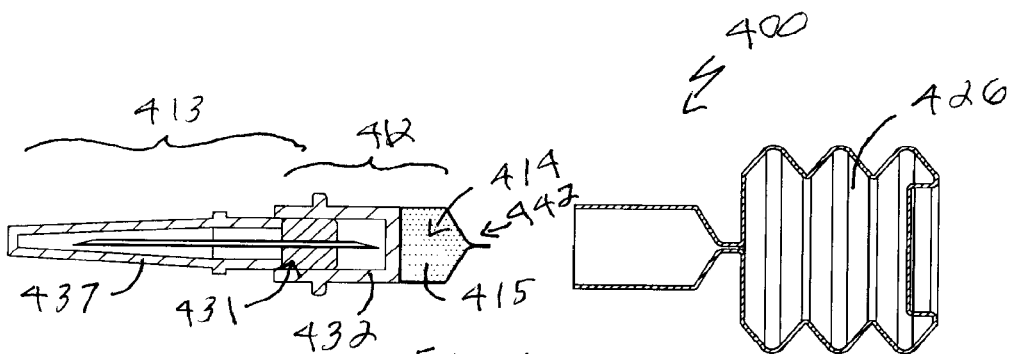
FIGS. 4a-4e demonstrate a further exemplary embodiment where the substance-insert is included in the applicator-insert.

Referring now to FIGS. 4a-4e a further exemplary embodiment is demonstrated where the applicator 413 is integrated with the substance-insert 412 (hereafter in this embodiment collectively referred to as the "substance insert") and introduced to the rest of the package 400 in the manufacturing process as one. FIG. 4a demonstrates an exploded section view of the pre-activated state of the package 400. The substance-insert 412 comprises a housing 432, a needle assembly 431 movable within the housing 432 (comprising a distal sharp-end for delivering the content of the package 400 to a subject, and a proximal sharp for piercing the housing 432 in order to establish fluid communication between the contents of the package 400 and the needle); and a needle protector 437 accommodated in the housing 432 and movable within the housing to manipulate the needle assembly 431 to displace backward and pierce the housing 432. The substance insert further comprises a flexible barrier in a form of a tubular pouch compartment having a proximal open end attached to the housing in a fluid tight fashion, and a distal end where the pouch seam is collapsed to seal to itself in a frangible seal fashion. The needle protector 437 provides protection from accidental needle-sticks and/or aseptic conditions to the needle assembly until the time of use.

Figure 4B:
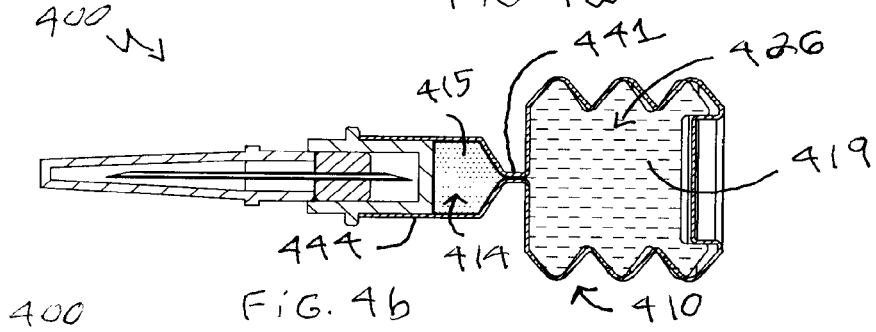

Referring now to FIG. 4b, the substance-insert comprises a pouch 442 formed from first and a second films attached to each other along their perimeter, and attached to the housing 432 to form the second compartment 414, which contains the second substance 415. A portion of the attachment between the first film and the second film of the second compartment 414 has a weakened seal force defining a frangible seal (sometimes referred to as peelable seal) section 441. The insert is accommodated at a neck section 444 in the front of the container 410. The housing provides an interface to the container 410 forming a firm fluid tight engagement. In one embodiment the neck portion 444 is further attached to the flexible barrier section 441 in a fluid tight fashion providing support to the susceptible portion of the flexible barrier, with the seal force between the flexible barrier and the container being stronger than the frangible seal force of the flexible barrier to itself. The frangible seal section 441 defines a separation between the first substance 419 and the second substance 415.

Figure 4C:
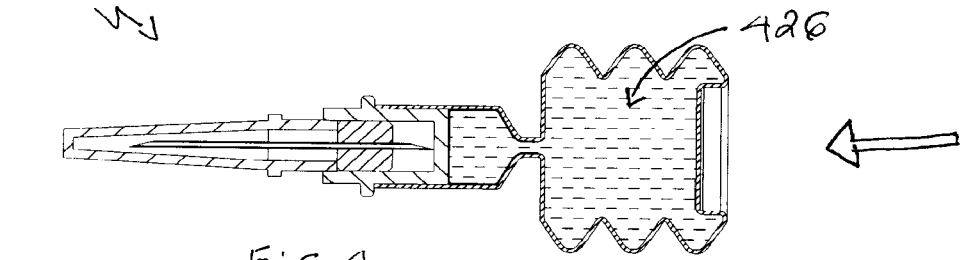

Referring now to FIG. 4c, the package 400 is demonstrated in the activation process after the first compartment 426 and the second compartment 414 have been merged to allow the first substance 419 and the second substance 415 to merge. Three preferred methods for causing the two compartments (426, 414) to merge will be described:

a) In the first method the first compartment 426 is pressurized by applying force to the bellows-shaped first compartment 426 in the direction of the arrow. The neck of the container 410 is attached to frangible seal section 441 in a fluid tight seal fashion such that the pressure in the first compartment 426 biases the neck to expand, thereby pulling apart the first wall and the second wall of the second compartment 414, resulting in separation of the frangible seal and merger of the two compartments and their contents.

b) In the second method the user pressurizes the second compartment 414 by pinching the second compartment 414 through deformation of the neck of the container 410, thereby pressurizing the flowable second substance 415 which forces the frangible seal 441 to separate and the first and second compartments (426, 414) to merge.

c) In the third method the neck of the container 410 is attached to frangible seal 441 section. The elongated thinned area of the neck where it is attached to the frangible seal 441 is compressed by pressing the two distal ends of this section toward one another causing them to collapse and arch away from each other thereby causing the frangible seal 441 to separate.

Figure 4D:
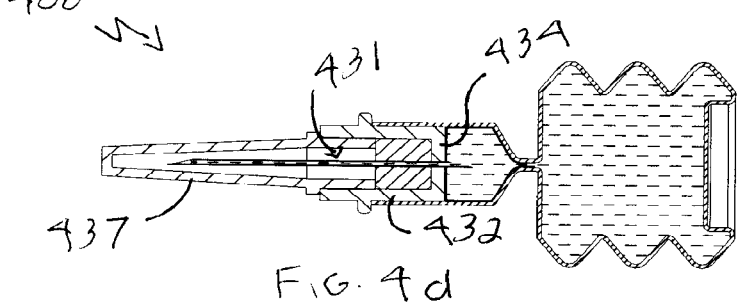

FIG. 4d demonstrates a subsequent step whereby the protector 437 is pushed back to cause the proximal sharp end of the needle assembly 431 to penetrate the thin membrane at the back of the housing wall 434 thereby establishing fluid communication with the contents of the package 400. The membrane of the housing 432 is preferably made from a polymeric material which is substantially resilient to allow penetration of the back sharp end of the needle with hand force, and maintain a fluid tight seal between the needle and the membrane.

Figure 4E:
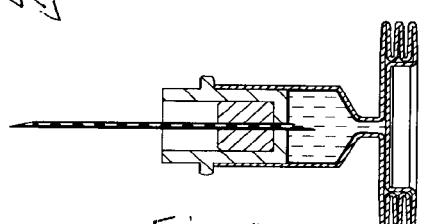

FIG. 4e shows the package 400 at the end of the delivery state. The protector is now removed and the bellows-shaped first compartment is collapsed to cause substantially complete expression of the product.

Referring now to FIGS. 5a-5h a further preferred package 500 is demonstrated where the applicator-insert 513 and the substance-insert 512 are combined. FIG. 5a provides a general perspective view of the package 500, showing the container having a bellows shaped first-compartment 526 on its back end, and a neck 544 for receiving and engaging with integrated insert 5121513. The insert comprises a needle protector 537 having 4 ribs 539 extending radially outwardly base. The four ribs are hollow as will better demonstrated in subsequent figures to accommodate reciprocal ribs at the needle hub 529. FIG. 5b demonstrates an exploded perspective view of the package 500 where the insert housing 532 and the needle assembly 531 are displaced from their position in the container 510. The needle hub 529 comprises a through hole for accepting the needle 527, four ribs extending 550 in a radial direction to communicate with the four hollow ribs 539 in the container 510, and a threaded portion 552 to communicate with reciprocal threading in the insert housing.

FIG. 5c demonstrates the integrated substance-insert 512/513. The integrated-insert 512/513 comprises a housing 554, the needle assembly 531, and a second compartment 514 in a form of a blister-pack, made from a flexible barrier. The needle assembly 531 comprises (1) the needle 527 having a distal sharp end for administrating the contents of the package 500 to a subject and a proximal end for piercing the second compartment and introducing the merged product to the needle 527; and (2) the needle hub 529 associated with the needle 527. The needle hub 529 is accommodated in the housing 532 and is engaged to the housing via a reciprocal thread on the internal wall of the housing and the external side of the needle hub 529, such that when the needle hub is turned it advances along the axis of rotation (mutual with the axis of the needle). The substance insert 512 comprises a flexible barrier in a form of a film portion 517 formed and sealed to itself by a frangible seal 555 to form a second compartment 514 filled with the second substance 515. The film portion 517 is supportably attached to the back end of the housing 532 along its perimeter 556. The housing is also referred to as "frame". The insert can be manufactured on a separate manufacturing line than the container and the integration of the package.

FIG. 5d demonstrates a side section view of the package 500 in the rest position. The integrated insert is accommodated in the container 510 in front of the first compartment 526, such that the frangible seal 555 of the second compartment 514 constitutes a flexible barrier between the first substance 519 and the second substance 515. The container 510 extends along the insert and forms a twist-off portion 522 around the needle 627. The twist-off portion 522 comprises hollow ribs that are engaged with the reciprocal ribs in the needle-hub 529 such that when the twist-off portion 522 will be turned (for removal) the needle assembly will turn along with it. The package can be manufactured in a BFIS seal line. The housing's external surface provides an interface for engaging the container in a firm fluid tight fashion.

Referring to FIG. 5e, the package 500 is demonstrated at a first activation step where the first and second compartments are merged to create a merged compartment 523. By squeezing the first compartment 526, in the direction of the arrow, the first substance 515 pressurizes causing the frangible seal of the second compartment 514 to separate, and for the two compartments to merge. Further squeezing of the first compartment 526 in the direction of the arrow causes the film portion 517 to extend until it firmly leans against the partition wall in the housing 532. The proximal sharp end of the needle assembly 531 is accommodated in a through hole in the partition wall of the housing 532, such that the tip of the needle is confined in said hole preventing it from piercing the film portion 517.

Referring now to FIG. 5f, the package 500 is demonstrated in a subsequent activation step. The twist-off portion 522 has been turned as the arrow indicates causing it to disengage from the rest of the container 510. The turning of the twist-off portion 522 caused the needle assembly 531 to turn and retract toward the merged compartment by way of threads 552, causing the proximal end of the needle 527 to project out from the partition wall of the housing 532 and pierce the film portion 517, thereby establishing fluid communication between the contents of the package 500 and the needle 527. In one embodiment the integrated insert is equipped with a seal that facilitates the fluid tight seal between the needle assembly 531 and the merged compartment.

Referring now to FIG. 5g, the package 500 is demonstrated at a subsequent activation step in which the twist off portion 522 is removed.

FIG. 5h demonstrates the package 500 during administration of the contents. A concaved section 553 in the back of the first compartment 526 is made to fit into the film portion 517 as the first compartment 526 is squeezed, thereby improving the express ratio of the package. It will be obvious to those skilled in the art that an alternative activation sequence may be applied, whereby, after stage 5f, the bellow is released allowing the film portion 517 to relax and displace away from the needle. Thereafter the protector is twisted-off thereby retracting the needle into the container. The package may then be squeezed to pressurize the product and cause the flexible barrier to extend toward the back sharp of the needle and cause it to rupture.

Figure 6A:
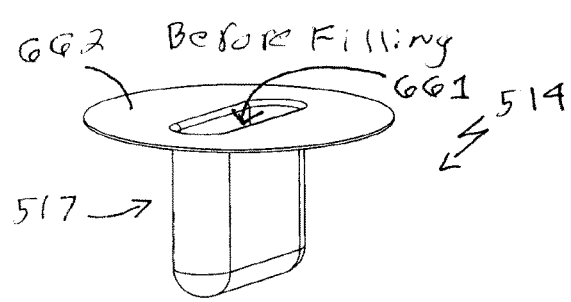
FIGS. 6a-6f demonstrate the details of one preferred fashion of making the film capsule for the embodiment of FIGS. 5a-5h.
Figure 6B:
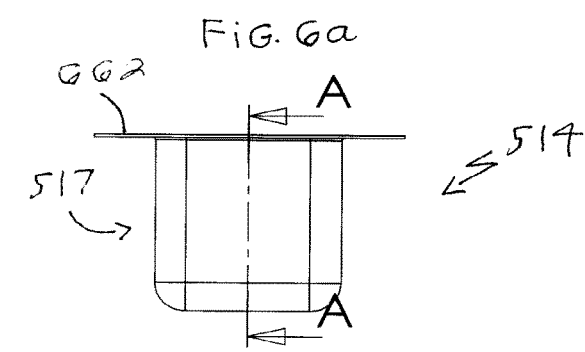
Figure 6C:
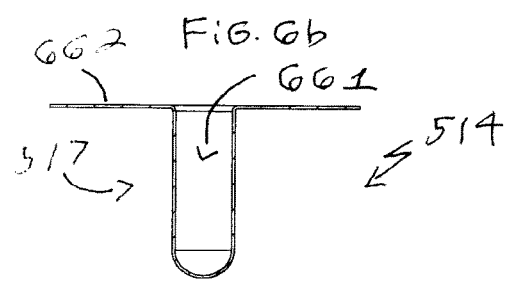
Figure 6D:
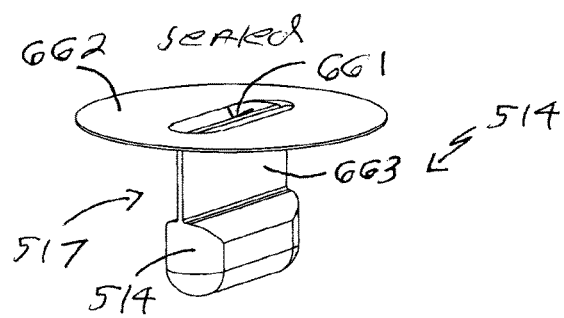
Figure 6E:
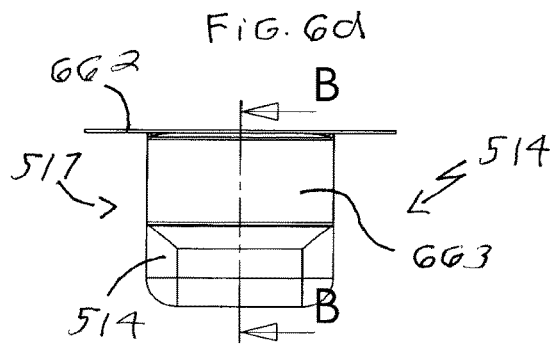
Figure 6F:
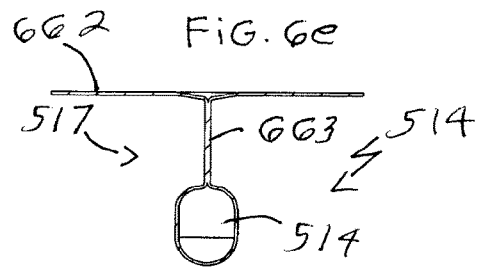

Referring now to FIGS. 6a-6f, a preferred design and method of manufacturing a second compartment 514 is demonstrated. FIGS. 6a, 6b, and 6c demonstrate different views of the flexible barrier in a fashion of a film portion 517 after it has been processed to have a flange portion 662 and a deep drawn cavity 661, having a proximal end proximal to the flange and a distal end. The pocket can be drawn by thermoforming, plug-assist forming, cold forming, or the part can be formed by blow molding, injection-molding, injection-blow-molding, blow-injection-molding, or other applicable molding or forming technologies known in the art. The second substance (not shown) is filled to the cavity at that stage. FIGS. 6d, 6e, and 6f demonstrate different views of the film portion 517 after the deep pocket 661 has been sealed across 663 to form the compartment 514. The proximal end of the cavity is made to collapse and seal to itself to form the second compartment at the distal end of the cavity. The sealing can be performed by various techniques including, heat-stake-welding, RF welding, vibration welding, ultrasonic welding, laser welding, bonding, gluing or any other techniques known in the art for forming a fragible seal. The seal 663 is a frangible seal that will be separated under the presence of pressure at either side of the film 617 (i.e the first or second compartments). The advantage of this design that it provides a smooth and flat flange portion 662 for connecting the film portion to the housing (532 in FIG. 5) in a fluid tight seal fashion. In a further embodiment a fluid transport device is associated with the distal end of the cavity.

While the embodiments in the figures above are demonstrated with a semi-rigid container it will be apparent to those skilled in the art that the approaches disclosed herein are applicable and advantageous in applications where the container or the first compartment are rigid such as a glass container, or flexible such as a bag.

Figure 7A:
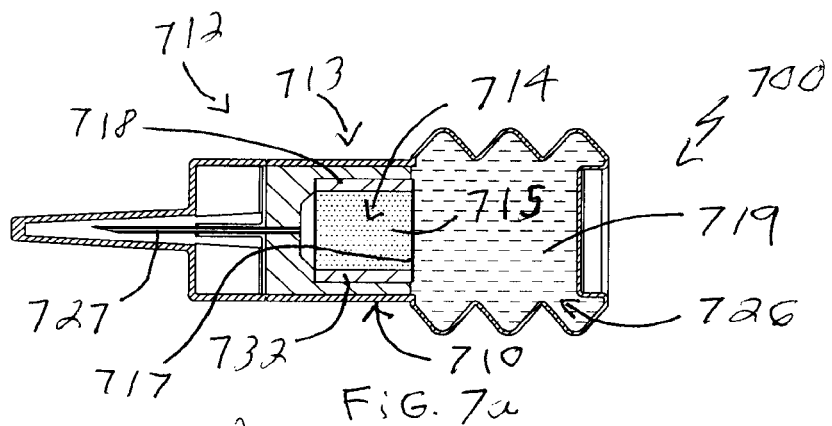
FIGS. 7a-7c demonstrate a further preferred embodiment where the flexible barrier is jeopardized during application, rather than prior to it.
Figure 7B:
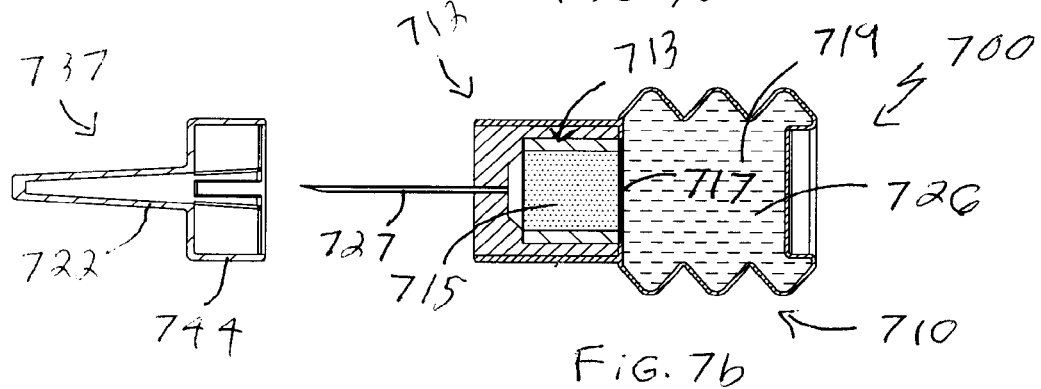
Figure 7C:
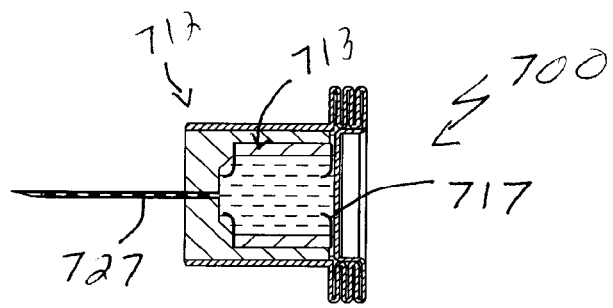

FIGS. 7a-7c demonstrate another exemplary embodiment of a package 700. The substance insert 712 includes the applicator (or fluid transport device) 713 and comprises a housing 732 (which may be considered a frame in this and the previous figures), a needle 727 attached to said housing, and a second compartment 714 for storing the second substance 715. The second compartment comprises a barrel 718 and a flexible barrier 717 sealing the two open ends of said barrel 718. Portions of said flexible barrier are supported by the barrel to define susceptible portions of the flexible barrier at the two ends of the barrel.

The insert housing provides an interface to the container 710. The container comprises a distal end shaped as a bellows to form the first compartment 726, and a neck 744 (FIG. 7b) that extends beyond the insert to form a twist off portion 722 in a form of a needle protector 737.

FIG. 7b shows the package 700 after the needle protector 737 has been removed.

Referring now to FIG. 7c, when the bellows is depressed the first product 719 and the second product 715 press on the susceptible portions of the flexible barrier 717. The support of the barrel 718 to the flexible barrier 717 translates the applied press on the flexible barrier to applied force on the susceptible sections of the flexible barrier causing them to rupture and permit the first and second substances to merge and be dispensed.

Other package embodiments will now be described with reference to FIGS. 8 through 27. Disclosed in these Figures (as above) are package constructs comprising a container for storing a first substance and at least one substance-insert for storing a second substance at least partially disposed within said container. The product-insert comprises a container interface for engaging said substance-insert with the container. The container comprises a first compartment for storing the first substance and the insert comprises a second compartment for storing the second substance. The second compartment comprises a flexible barrier separating between the first and second substances, and having a susceptible portion that is supported in a way that translates applied pressure to the flexible barrier or certain deformation to the package into applied force to the susceptible portion of the flexible barrier, which in return jeopardizes the integrity of the flexible barrier and allows the substances to merge. When the flexible barrier is jeopardized the package is sometimes referred to hereafter as open or activated. Before breaking the integrity of the flexible barrier the package is sometimes hereafter referred to as sealed or pre-used. The susceptible portion of the flexible barrier is sometimes referred to hereafter as a "valve" having an "open" and "closed" states.

In some of the remaining embodiments (as above) the substance-insert further comprises a frame for supporting the second container. The frame facilitates the introduction of the substance-insert to the container during manufacture. In some arrangements the frame provides the support to the susceptible portion of the flexible barrier. In some arrangements the frame provides the container interface. The package is made such that certain deformation of the container, caused by external manipulation of the package, will jeopardize the integrity of the flexible barrier and allow the first substance and the second substance to merge. In some arrangements the frame is substantially resilient to correspond to applied deformation to the package by corresponding deformation to the frame which results in an applied force to the susceptible portion of the flexible barrier which jeopardize the integrity of the flexible barrier. In some arrangements the frame is substantially rigid to support the susceptible portion such that, when pressure is applied to the flexible barrier (due to deformation of the container), it is translated to an applied force to the susceptible portion, jeopardizing the integrity of the barrier.

In some arrangements the package further comprises a fluid transport device for delivering the merged contents of the package to a target location in a desired fashion after the substances were allowed to merge. In some arrangements at least a portion of the fluid transport device is formed in the container. In some arrangements at least a portion of the fluid transport device is formed in the substance insert. In some arrangements at least a portion of the fluid transport device is formed in the frame. In some embodiments at least a portion of the fluid transport device is formed in the second compartment. In some embodiments at least a portion of the fluid transport device is an insert associated with at least one of the container, product-insert, second compartment, and the frame.

In some arrangements the product-insert comprises more than one compartment. In a preferred embodiment of the container, at least a portion of this compartment is a flexible barrier made from a film or a foil (hereafter sometimes referred to together as "web").

The web is sealed around its edges to form a wall of said compartment, and at least a portion of said seal is a frangible seal which can be separated under the presence of sufficient peeling stress and serves as a single-use valve. The web extends beyond the frangible seal sections to form a flange shaped membrane, which is arranged such that it will deliver force to the frangible seal in the presence of pressure or particular deformation of the container, and jeopardize the Integrity of the flexible barrier. In some arrangements a frame is associated with the flange and provides the necessary support such that the pressure in the container or the deformation of the container will be transferred to the flange in the appropriate way to cause the flange to open.

In some arrangements at least one of the compartments of the container is pre-filled with a substance. In some arrangements at least one compartment is filled at a later stage. In some arrangements the substances of at least two compartments are merged to form a product. Applications for the mixing containers include drug compounding, vaccine reconstitution, beverage or food preparation, lab applications, sample preparation, adhesives, cosmetics, etc.

In some applications the container is used in an analytical process in which one of the compartments contains an instrument for measuring a property of a sample, which instrument may be a compound or probe. In some applications the instrument is introduced through a port to the compartment.

In some arrangements the area of the container extending from the container interface and away from the first compartment forms a third compartment substantially encapsulating the second compartment. The third compartment provides a mean for creating a desired controlled environment around the second compartment and substantially isolates it from the surrounding environment or the environment of the first compartment. In some arrangements a drying agent such as a desiccant in disposed in the third compartment to maintain a dry environment substantially surrounding the second compartment. This is of a particular advantage where the second product is a dry substance such as a food or pharmaceutical substance which perish or loose potency due to humidity. In another arrangements the third compartment contains inert gas or liquid, or a thermally isolating filler. In some arrangements said third compartment accommodates a label such that the label can not separate from the package, and is less exposed to weathering or physical damage.

Methods are also described or otherwise contemplated for manufacturing multi-compartment containers using a Blow-Fill-Seal technology.

Figures 8A, 8B:
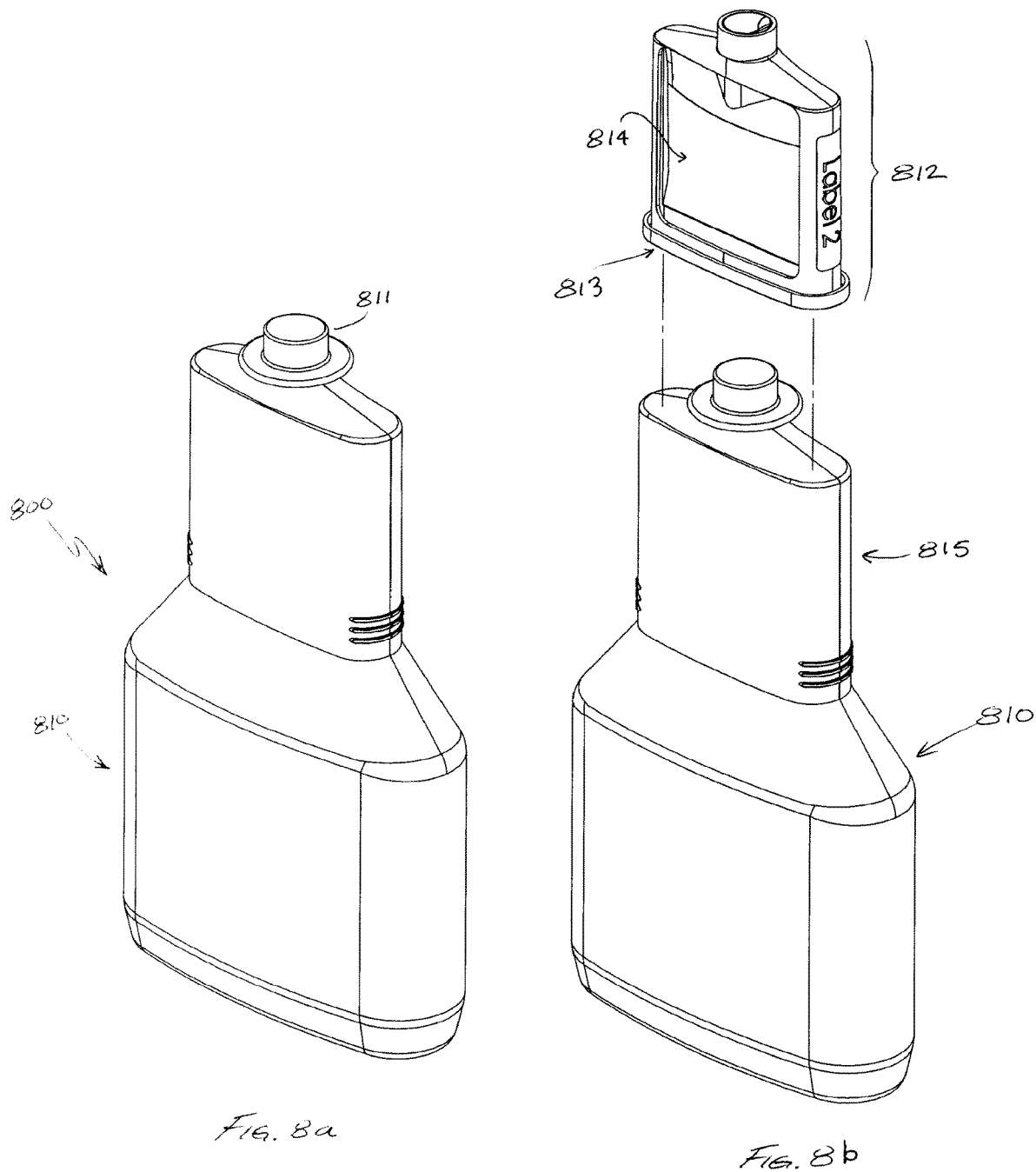
FIG. 8a-8b show general views of an exemplary package and the product-insert thereof.

FIG. 8a shows a package 800 in the form of a hermetically sealed container 810 having a general shape of a bottle. The container 810 comprises a fluid transport device in the form of a closure 811 at one end for pouring the content of the container or introducing a substance into the container 810. The container can be made from different materials including thermoplastics such as Polypropylene (PP) or Polyethylene (PE) or a composition of several materials such as a multilayer plastic that includes Polyethylene or PVC layers, and EVOH layer to provide higher barrier to moisture or oxygen transmission.

The container 810 can be made by several technologies including injection molding, gas-assist-injection-molding, injection-blow-molding, blow-molding, blow-fill-seal technology, vacuum forming, form-fill-seal, extrusion or sleeve forming, or any combination of the above. The container 810 holds a first substance in first compartment.

FIG. 8b shows an exploded view of the container 810 revealing a substance-insert 812 which is accommodated in the neck-portion 815 of the container 810. The substance-insert 812 comprises a 2nd compartment 814 and a frame 813. The 2nd compartment is made to store a 2nd substance separately from the 1st substance. As will be demonstrated in the following Figures, the 1st substance and the second substance can be mixed by external manipulation of the container without breaching the integrity of the aseptic seal of the container 810.

FIG. 9 shows different views of the second compartment 814. FIG. 9a shows a general view of the 2nd compartment 814. The second compartment 814 comprises a flexible barrier in a form of a pouch 921 made from a film or a foil (each and together sometimes referred to as "web"). The pouch can be formed by several processes including: a) two flat or formed pieces of web sealed together along a sealing line, b) a single piece of web, flat or formed, folded and sealed along a sealing line c) an extruded or blown web sleeve flattened and sealed along a sealing contour. A fitment 922 is accommodated between the two layers of film that form the pouch 921 providing a portion of the fluid transport device in a form of a port 923 to the 2nd compartment 814. A frangible seal 924 seals along an edge of the pouch 814, defining a susceptible portion of the flexible barrier, and the margin of the web beyond the frangible seal 924 is formed into a form of a flange 925. The web can be made from several materials including mono layer film such as PVC, PP or PE, a multi layer film such as PE/PCTFE for high oxygen and moisture barrier; or foils such as AL/EVA. The pouch 921 further comprises a label 928 or directly printed material.

Figure 9A:
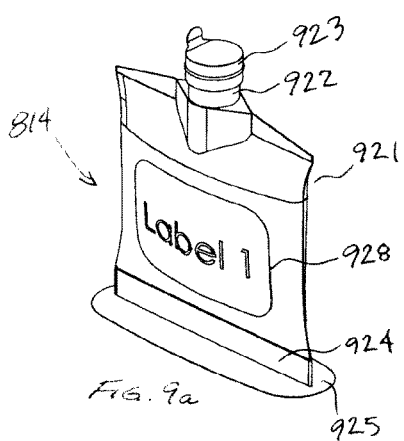
FIGS. 9a-9f show several views of an exemplary embodiment of the second container for the packaged product.
Figure 9B:
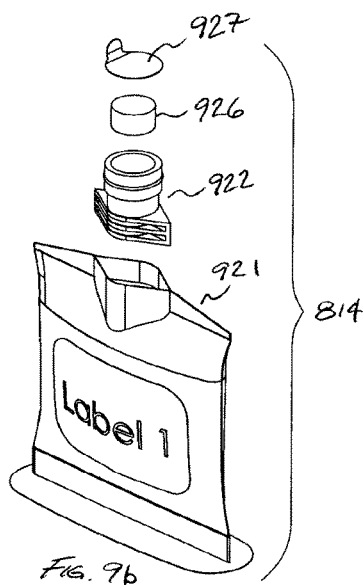

FIG. 9b shows an exploded view of the second compartment 814. The fitment 922 confines a septum valve 928 for introducing a sharp object such as a gauge needle or an infusion set spike to the second compartment 814 in a fluid tight manner. The septum 926 is topped with a foil portion 927 that maintains a high barrier Integrity to the second compartment 814 as rubber septums suffer from relatively high moisture and oxygen transmission. The fitment 922 is made from a material that has good compatibility for welding to the pouch's web, or compatible to the adhesive that seals the fitment 922 to the pouch's web. In some embodiments the fitment provides other types of ports to the 2nd compartment 814 including a spout for a replaceable threaded cap, a snapped on cap, or single use tear-off or twist-off caps, a Luer or Luer-Lock connector, other type of connectors, a needle, a droplet nozzle, a spray or mist nozzle, a topical applicator, or a hose or a tube leading to one of the above ports.

Figure 9C:
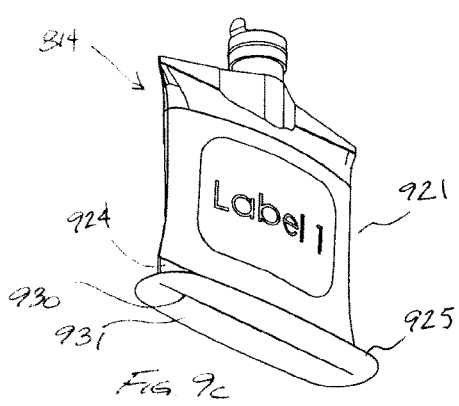

FIG. 9c shows a general view of the second compartment 814 from a different angle. The frangible seal 924 shows as a sealing line mark 930 on the flange 925. The frangible seal is such that it would separate at a predefined separation tension (i.e. applied force). The frangible seal 924 is such that a pull-off force between the one side web of the seal 924 and the second side web of the seal will cause it to separate and infringe the integrity of the pouch 921 establishing fluid communication with the external side of the flange. The pull-off force on the walls of the frangible seal can be created by a) fluid pressure in second compartment 814, b) matter pushing from the interior of the container 814 against the frangible seal, c) fluid pressure presented at the external side 931 of the flange 925, d) matter pushing from the external side 931 of the flange 925 against the flange 925 and/or the frangible seal 924, or e) merely a pull apart force on the fringes of the flange 925 (as is done in the practice of opening a snack pouch). In this manner the susceptible portion of the flexible barrier in the form of a frangible seal acts as a single-use valve and will hereafter sometimes be referred to as a 'valve'.

Figure 9D:
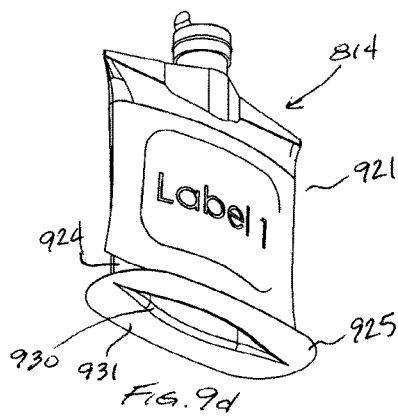

FIG. 9d shows the second compartment 814 after the frangible seal 924 has been separated (i.e. valve opened), establishing fluid communication between the 2nd substance and the external side 931 of the flange 925. The following figures will demonstrate that by opening the valve the first compartment and the second compartment merge, and the second substance is allowed to merge with the first substance in the first compartment.

Figure 9E:
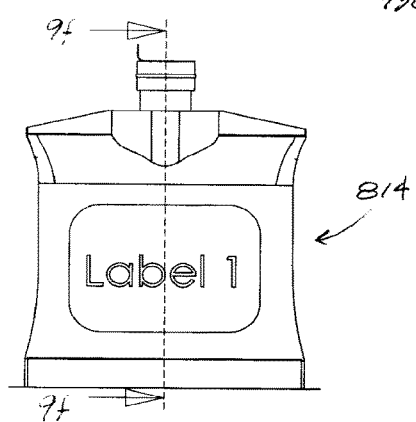
Figure 9F:
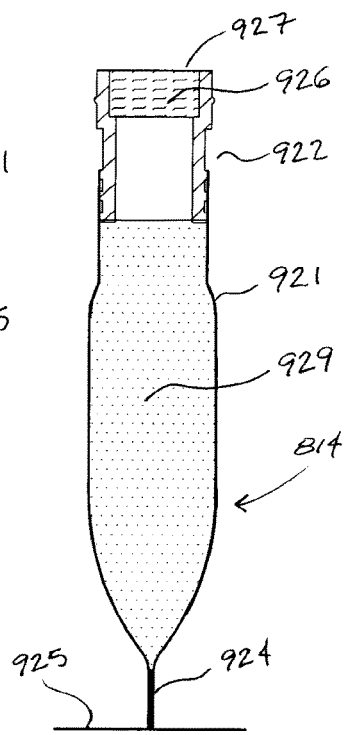

FIG. 9e shows a front view of the second compartment to provide orientation of the section view of FIG. 9f.

FIG. 9f shows a section view of the second compartment 814 revealing the 2nd substance 929 confined between the pouch walls 921, the fitment 922, and the frangible seal 924. The 2nd substance 929 can be one substance or a combination of substances in various forms including gas, liquid, solution, suspension, gel, paste, loose powder, compressed powder, pellets, granules, solid, or a combination of the above. In some preferred embodiments the 2nd substance 929 is a pharmaceutical ingredient or vaccine in a dry powder form.

FIG. 10 demonstrates a different configuration of the second compartment 1031.

Figure 10A:
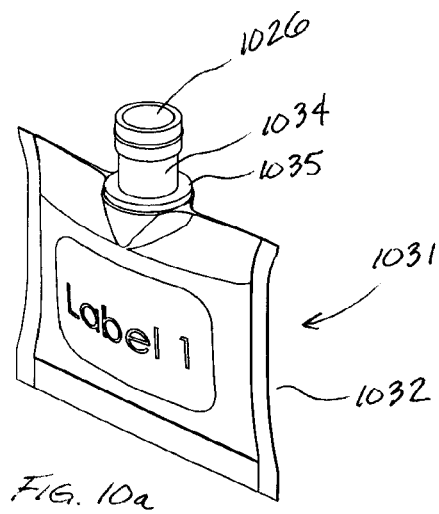
FIGS. 10a-10c show a further exemplary embodiment of the second container.

FIG. 10a shows a general view of the second compartment 1031. A portion of the fluid transport device in the form of a fitment 1034 comprises a flange 1035 that is attached to the external side of the pouch 1032 such that the fitment 1034 and the septum 1026 do not come in contact with the 2nd substance 1029 until the time of use. The pouch 1032 is made by folding a continuous web piece such that the area where the fitment 1034 is attached is flat and clean of any seam lines.

Figure 10B:
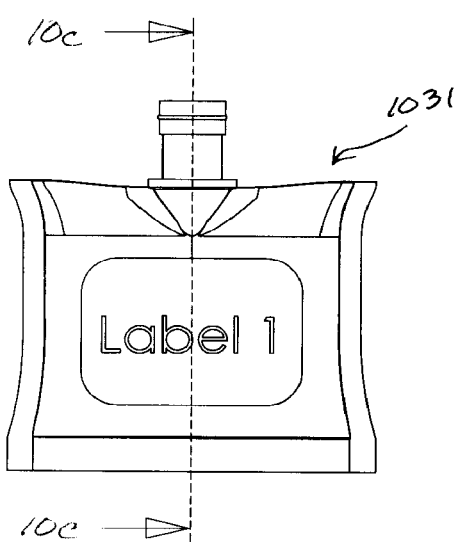
Figure 10C:
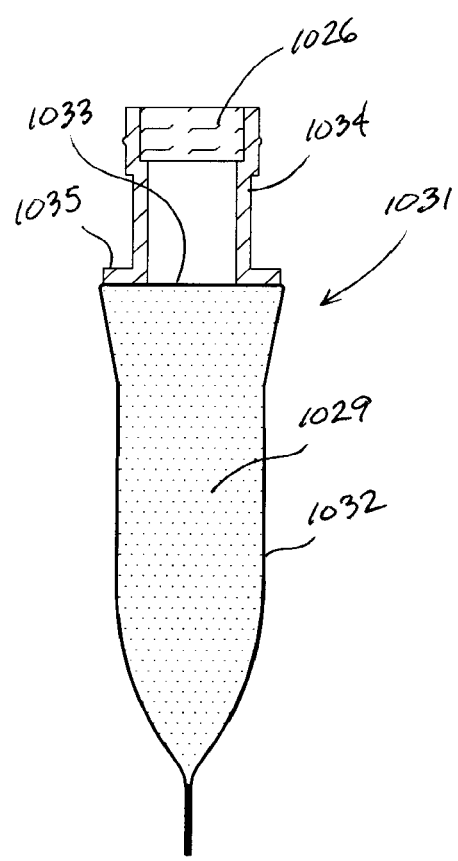

FIG. 10b shows a front view of the second compartment 1031 providing orientation of the section view in FIG. 10c.

FIG. 10c shows a section view of the second compartment 1031 showing how the pouch 1032 provides a seamless surface 1033 for attaching the flange 1035 of the fitment 1034. A needle or a spike introduced to the container 1031 through the septum 1026 will pierce the portion of the wall 1033 and establish fluid communication with the 2nd substance 1029.

FIG. 11a shows the second compartment 814 associated with the frame 813, together forming the substance-insert 812. A desiccant capsule 1118 is associated with the frame.

FIG. 11b shows an exploded view illustrating how the second compartment is introduced to the frame. The flange 925 of the pouch 921 seals against the flange 1141 of the frame 813. The fitment 922 is accommodated at an opening 1142 of the frame 813. The frame 813 provides the second compartment a rigid structure that facilitates the introduction and accommodation of the substance insert 812 in the first container. The frame further provides support to the susceptible portion of the flexible barrier to facilitate the opening of the frangible seal 924 as will be described below.

FIG. 11c shows a general view of the substance insert 812 before the frangible seal is separated. The flange 1141 of the frame 813 has the form of an oval or elliptical ring such that when the points on the major axis of the ring 1143' and 1143" are displaced toward each other (or the center) the areas of the ring closer to the minor axis 1144' and 1144' are displaced away from each other thereby pulling-off the walls of the pouch 921 at the flange 925 area, causing the frangible seal 924 to separate. Where substance is pushing against the external side 931 of the flange 925 the frame firmly holds the fringe of the flange and facilitates concentration of the force on the flange 925 to separate the frangible seal 924.

FIG. 11d shows the substance insert 812 when the areas of the flange 1141 of the frame 813, along the major axis ends 1144' and 1144" are deformed toward each other, causing the frangible seal 924 to separate, opening the valve to the second container 814. A label 1145 can be accommodated on the frame. Information can also be printed or otherwise applied directly to the frame.

FIG. 11e shows the substance insert 812 when it is not deformed, providing orientation for the section view of FIG. 11g.

FIG. 11f shows the insert when the flange 1141 is deformed along the major axis by applying force in the direction of the arrows 1146' and 1146' at areas 1143' and 1143" of the flange 1141, to cause the valve to open. It should be apparent to those skilled in the art that nothing in the description above of the substance insert 812 is limiting to a particular shape, form, or size, and that the substance insert 812 can be designed to fit different container forms and applications. The frame of this particular embodiment can be made from a semi-rigid plastic with or without the support of metal elements that can improve its behavior.

FIG. 11g shows a section view of the substance insert 812 to depict how the second compartment 814 is accommodated in the frame 813 and how the susceptible portion of the flexible barrier is being supported by the frame.

FIG. 12a shows the container of an exemplary embodiment of the package of the in a non-deformed state. FIG. 12a provides orientation for the section view of FIG. 12b. The 1st container 810 is made by a blow-fill-insert-seal process (BFIS). Blow-Fill-Seal (BFS) technology refers to the manufacturing technique used to produce liquid filled containers and is considered to be the superior form of aseptic processing in the packaging of pharmaceutical and healthcare products. The basic concept of Blow-Fill-Seal (BFS) is that a container is formed, filled, and sealed in a continuous process without human intervention, in a sterile enclosed area inside a machine. Thus this technology can be used to aseptically manufacture sterile pharmaceutical liquid dosage forms. The process is multi-stepped. Firstly, pharmaceutical-grade plastic resin is vertically heat extruded through a circular throat, to form a hanging tube called the Parison. This extruded tube is then enclosed within a two-part mold, and the tube is cut above the mold. The mold is transferred to the filling zone, or sterile filling space where filling needles mandrels are lowered and used to inflate the plastic to form the container within the mold. Following the formation of the container, the mandrel is used to fill the container with liquid. After filling the mandrels are retracted and a secondary top mold seals the container. All actions take place inside a sterile shrouded chamber inside the machine. The product is then discharged to a non-sterile area. Blow fill seal technology reduces personnel intervention making it a more robust method for the aseptic preparation of sterile pharmaceuticals. Generally the BFS plastic containers are made up of polyethylene and polypropylene. A slight variation to the BFS process is called Blow-Fill-Insert-Seal (BFIS) in which after the liquid filling an insert is introduced to the container, before the secondary top mold seals the container. Typical inserts include rubber septums, connectors, and needles, and one manufacturer of such products is Rommelag Kunststoff-Maschinen Vertriebsgesellschaft mbH from Waiblingen, Germany.

FIG. 12b shows a section view of the package 810 of FIG. 12a. The first substance 1251 fills a portion of the container's first compartment. The first substance 1251 can be a single substance or a combination of several substances in various forms including gas, liquid, suspension, gel, paste, loose powder, compressed powder, pellets, granules, solid, or any combination of the above. The substance insert 812 is accommodated at the neck portion 815 of the container 810, such that the port 1142 is aligned with a tear-off closure 811 of the container 810. The external face of the flange 1141 provides a container interface. Flange 1141 of frame 813 seals in a fluid tight fashion against the wall of the container 810 such that a third compartment 1252 is formed which is free of the first substance 1251 or the second substance 929, such that the first substance 1251 cannot reach the area around the pouch 814. The pouch's flange 925 separates between the first substance 929 and the second substance 1251 in a fluid tight fashion. In some embodiments a desiccant capsule (1118 in FIG. 11a) is introduced in the third compartment 1252 to reduce moisture that could transmit into the second compartment 814.

FIG. 12c shows the 1st container 810 when it is deformed in the direction shown by the arrows 1146' and 11465" in the neck section 815, which in return deforms the flange (1141 in FIG. 11) causing the opening of the second compartment 814 (opening of the valve) as demonstrated in FIG. 11.

FIG. 12c provides orientation for the section view of FIG. 12d.

FIG. 12d shows a section view of the 1st container 810 after the valve of the second compartment 814 has been opened and the 2nd substance 929 (not shown) was allowed to merge with the first substance 1251 (not shown) creating the product 1253. A process for introducing a first substance with a second substance without jeopardizing the aseptic integrity of the container 810 is thus demonstrated.

The third compartment 1252 can accommodate labels or printing information which is internal to the container 810, but is separated from the first substance 1251 or the second substance 929 or their product 1253, and is visible through the clear or semi-clear wall of the container 810. This creates a unique opportunity to incorporate labels in a protected fashion which can prevents label from being weathered, damaged, misplaced or replaced.

In one embodiment the package is an IV infusion bottle wherein the first substance is water for injection (hereafter as commonly referred to in the art "WFO") and the second substance is a pharmaceutical in a thermostable dry-powder form (such as insulin, antibiotic, interferon, biologics such as imiglucerase, and oncology drugs such as gemcitabine) which are mixed to create an infusion solution prior to administration to a patient.

In one embodiment the package is a vaccine bottle where the first substance is WFO and the 2nd substance is a vaccine in a thermostable powder form where the first and second substances are mixed just prior to use and the product is drawn with a needle to a syringe and then injected with the syringe to the patient.

In one embodiment the first substance and the second substance are hormones that should be combined just prior to a treatment.

In one embodiment the product 1253 is a beverage and the second substance 929 is an additive such as a vitamin that is added to the beverage 1251 just prior to consumption.

In one embodiment the product 1253 is a baby formula where the first substance is water and the second substance is a baby formula powder.

In one embodiment the container is at least part of an analytical system where at least one of the compartments of the package is associated with a probe or a measuring element that provides an indication of the product.

FIG. 13 shows the package of FIG. 12 ready for use. The closure (811 in FIG. 1) has been removed by a twist off action, and the foil protection (927 in FIG. 9b) has been peeled off, and the fitment 922 is now ready to accept a spike of an infusion tube set. The package is placed with the outlet port 923 pointing down and the product 1253 will flow out by the suction force from the tube set (either forced pumping or gravity). The container walls will collapse inward to compensate for the depleting product 1253. In a further embodiment the container 810 can be pierced to allow air to compensate for the depleting content 1253. It will be apparent to those skilled in the art that other methods of introducing air into the container 810 are possible including ports with membranes that prevent bacteria from penetrating the container 810.

FIG. 14 shows a preferred embodiment where an oval actuator ring or annulus 1471 is mounted on the neck 815 of the container 810. The ring serves to facilitate deformation of the neck 815 of the container 810 to cause the valve to open and the mixing action described in previous Figures. FIG. 14a shows the pre-activation position where the major axis of the ring 1471—between points 1472' and 1472"—is aligned with the major axis of the neck 815—between points 1473' and 1473"—which represent the major axis of the frame's flange (1143' and 1143" FIG. 11f). FIG. 14b shows the mixing position of the package where the ring 1471 is turned a quarter turn such that its minor axis span between points 1474' and 1474" forcing the major axis points of the container's neck 1473' and 1473" toward the center and the container to deform, causing the mixing action described in former Figures. It will be apparent to those skilled in the art that other external devices can be implemented to facilitate the manipulation of the container to the open state.

FIG. 15 shows a further preferred embodiment in which the twist-off closure 1581 of the container 1580 extends substantially toward the flange to the root of the neck section 1515, such that after opening a significant portion of the substance insert 1512 is exposed. In one embodiment the removable portion 1581 is an opaque cap to protect the second substance (such as 929 in FIG. 9f) in the product-insert 1512 from exposure to light, and the pouch 1521 is clear to allow visual inspection of the contents after the removal of the removable portion 1581. In one embodiment the twist-off removal action of the removable section 1581 deforms the container 1580 in a similar manner that the oval ring 1471 does in FIG. 14b thus causing the mixing action of the first substance and the second substance. In one embodiment the removable section 1581 is rigid such that the deformation of the frame for the mixing action can only be performed after the removal of the removable section 1581, providing a means for preventing accidental mixing.

FIG. 16 shows a preferred embodiment of a package where the substance insert is partially inserted into the container. The container can be made using a blow-molding, injection-molding, vacuum forming, film sleeving or other processes known in the art, and the substance insert 1612 is introduced to the opening of the container 1690 during, or after the walls of the container 1690 has been formed.

FIG. 17 shows a preferred embodiment where the container 1700 is in the form of a tube. Referring to FIG. 17a, the walls of the container 1701 are commonly produced by injection molding, and the open end of the tube 1701 is sealed after the insert 1712 and the first substance 1751 have been introduced into the tube 1701. Referring to FIG. 17b, the flange 1741 is sealed against the tube wall 1701 by one or more of the techniques know in the art including heat welding and/or press-fit.

FIG. 18 shows a further preferred embodiment where the substance insert 1812 is accommodated in the container 1810 remotely from the fluid transport device which is implemented in the first compartment.

FIG. 19 shows a further preferred embodiment where the substance insert 1912 is reduced to an oval flange 1941, comprising a container interface which is supporting a film barrier 1921 that has a frangible seal 1924 on one end and it expands into a flange shape 1925 on the other end. The substance insert 1912 forms a susceptible barrier between the first substance and second substance that are confined directly in the first container walls 1922. The frangible seal will rupture when the container 1920 is deformed in a similar fashion described in former Figures.

FIG. 20 shows a further embodiment where the insert is reduced to a flexible barrier that divides the container 2030 into a first compartment for the first substance 2051 and a second compartment for the second substance 2029. The insert comprises a flange 41, comprising a container Interface that seals against the walls 2031 of the container 2030 and a membrane 2032 extends inwardly to form the barrier and is supported by the walls of the container. A notch (score) 2033 is located on the membrane 2032 and will rupture when the container is deformed. The insert can be made from various materials including molded plastics or sheet metal.

FIG. 21 shows a further preferred embodiment where the rupturable separation 2142 is integrally molded with the walls 2141 of container 2140. A notch 2143 in the separation causes the separation 2142 to rupture when the container 2140 is deformed.

FIG. 22 shows an embodiment similar to embodiment of FIG. 17 with the exception that the substance insert 2212 includes a filter membrane 2252 that covers the external side of the flange 2227. The filter 2252 allows mixing of the first substance 2251 with the second substance 2229 but prevents larger objects (such as solid particles, suspended particles, large molecules or live cells) from penetrating from one substance to the other substance. In one embodiment the filter 2252 is a semi-permeable membrane that prevents gas or liquid phase from transporting across the membrane. In one embodiment the filter is an active membrane that causes chemical or physical separation of matter. In a further embodiment one of the compartments contains an analytical instrument and the membrane allows for specific materials to cross and reach said instrument.

Figure 23:
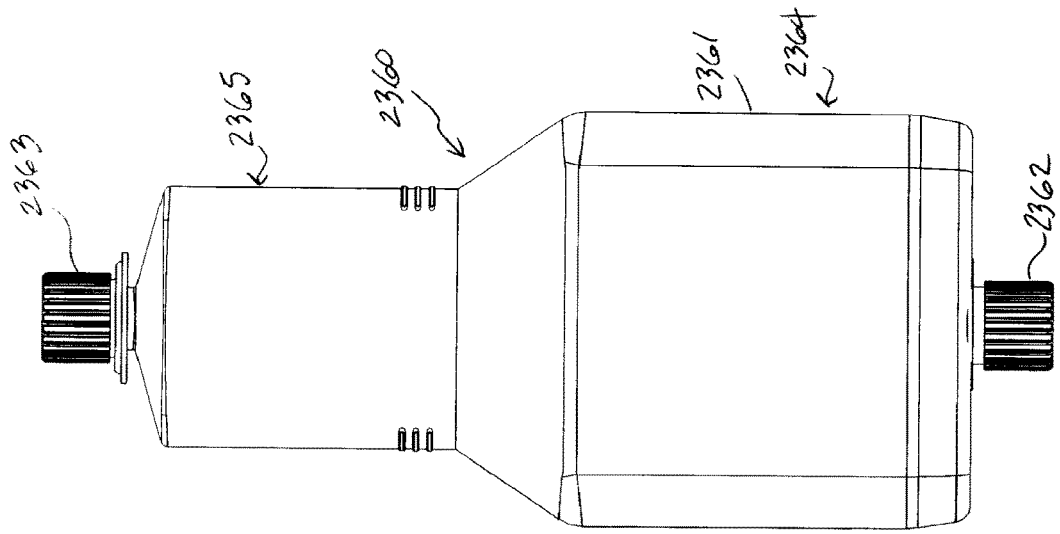
FIG. 23 shows an exemplary embodiment where the first-compartment and the second-compartment comprise a screw-cap port.

FIG. 23 demonstrates a further preferred embodiment of a package where the container 2360 comprises replaceable screw-cap 2362 for the first compartment 2364, and a replaceable screw-cap 2363 for the second compartment 2365. The caps allows for filling the substances during manufacture or by the user, adding matter (such as additives, reagents, samples, etc.) to the substances or to remove the first or the second substances or the product. In a further embodiment the caps are used to introduce, observe, or remove an analytical or diagnostic instrument. It will be apparent to those skilled in the art that various type of ports known in the art can be implemented in place of the screw-caps, and any number of ports can be implemented with the first and the second container.

Figure 24:
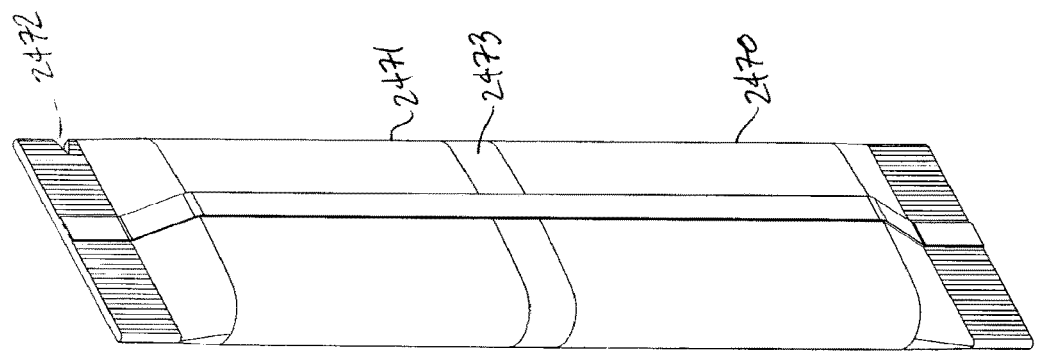
FIG. 24 shows an exemplary embodiment where the container is made from a sleeved web.

FIG. 24 shows an embodiment where the container is made from a web sleeve 2471. A tear-off notch 2472 facilitates the removal of the end portion 2473 to allow the user to reach the product. The flange of the frame is accommodated in the sleeve and its container interface is heat sealed to the sleeve 2471 after insertion at the welding area 2473.

Figure 25:
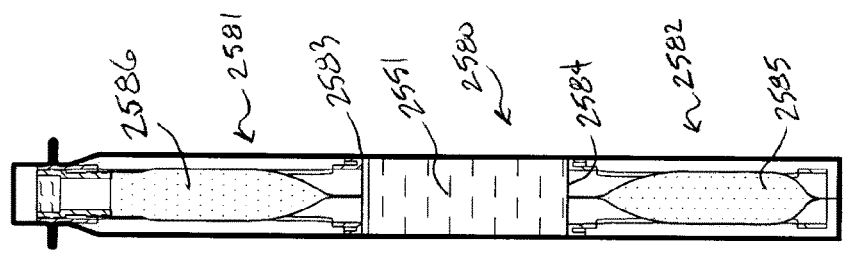
FIG. 25 shows an exemplary embodiment where the package comprises two substance-inserts.

FIG. 25 shows an embodiment with a second insert such that the container 2580 can hold three substances. Fluid communication is established between the first compartment 2581 and the second compartment 2582, and the first compartment 2581 with the third substance compartment 2583 in the same fashion described in the context of FIG. 12. It would be apparent to those skilled in the art that any number of inserts can be introduced in series or in parallel in the container.

Figure 26:
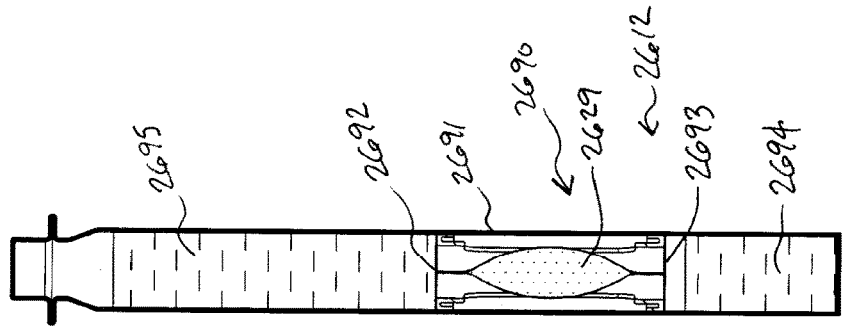
FIG. 26 shows an exemplary embodiment where the package comprises a substance insert with two valves.

FIG. 26 shows an embodiment of a package where the container 2690 contains a substance insert 2612 with valves on the first end and on the second end. The first valve 2692 separates the second substance 2629 from the first substance 2695, and the second valve 2693 separates the second substance 2629 from the third substance 2694. The valves are operated by similar means as the valves of the former figures. It will be apparent to those skilled in the art that the substance insert 2612 may include any number of valves, and that any number of such inserts may be included in the packaged product.

Referring now to FIG. 27, another embodiment of a package is shown. Referring to FIG. 27a, the web 2701 forms the second compartment 2702 as in FIG. 11 and it extends beyond the flange section to provide the walls of the first compartment 2703. The frame 2713 is attached to the first compartment and supports the second compartment 2702 as in FIG. 12.

FIG. 27b provides orientation for section view 27c.

FIG. 27c shows how the web 2701 forms the second compartment 2702 and extends beyond the flange 2725 to form the first compartment 2703.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A packaged product comprising:
  a. a container comprising a first compartment configured for storing a first substance; and
  b. a substance insert comprising:
    a flexible web wall defining a second compartment configured for storing a second substance, the flexible wall comprising a frangible seal that defines a susceptible region;
    a frame extending along the second compartment to provide mechanical support to the second compartment, the frame comprising a frame flange having an external face providing a container interface that substantially follows a shape of the container along an interface plane having a first axis and a second axis perpendicular to the first axis;
    wherein the flexible web wall extends from the frangible seal in a first direction to form the second compartment, and in a second direction perpendicular to the first direction and to the container interface to form a webbing flange that is connected to the frame flange; and wherein the substance insert is at least partially disposed within the container such that the susceptible region separates the first compartment and the second compartment; and wherein the container interface is disposed inside the container such that inward deformation of the container along the first axis causes corresponding deformation of the container interface along the first axis and causes the container interface and the webbing flange to deform outwardly substantially along the second axis, thereby manipulating the susceptible region to open causing the frangible seal to peel and jeopardize the integrity of the second compartment, thereby allowing first substance and second substance to merge.

2. The packaged product of claim 1 wherein the substance insert further comprises a port configured for dispensing the merged first substance and second substance.

3. The packaged product of claim 1 wherein the frame provides a port for dispensing the merged first substance and second substance.

4. The packaged product of claim 1 wherein the container interface forms a fluid tight seal with a wall of the container to thereby establish a third sealed compartment around the second compartment.

5. The packaged product of claim 4 wherein a modified environment is established in the third compartment by containing at least one of a desiccant and a gas.

6. The packaged product of claim 1 wherein the flexible web wall comprises at least one of a film and a foil.

\* \* \* \* \*